United States Patent
Igarashi

(10) Patent No.: US 9,657,040 B2
(45) Date of Patent: May 23, 2017

(54) CYCLIC SILOXANE COMPOUND, ORGANIC ELECTROLUMINESCENCE DEVICE, AND USE OF THE SAME

(75) Inventor: Takeshi Igarashi, Chiba (JP)

(73) Assignee: SAMSUNG ELECTRONICS CO., LTD, Gyeonggi-Do (KR)

( * ) Notice: Subject to any disclaimer, the term of this patent is extended or adjusted under 35 U.S.C. 154(b) by 1454 days.

(21) Appl. No.: 12/447,590

(22) PCT Filed: Oct. 31, 2007

(86) PCT No.: PCT/JP2007/071253
§ 371 (c)(1),
(2), (4) Date: Apr. 28, 2009

(87) PCT Pub. No.: WO2008/053935
PCT Pub. Date: May 8, 2008

(65) Prior Publication Data
US 2010/0060150 A1 Mar. 11, 2010

(30) Foreign Application Priority Data
Nov. 1, 2006 (JP) .................. 2006-298074

(51) Int. Cl.
*H01J 1/63* (2006.01)
*C07F 7/08* (2006.01)
(Continued)

(52) U.S. Cl.
CPC ............... *C07F 7/21* (2013.01); *C09K 11/06* (2013.01); *H01L 51/0094* (2013.01);
(Continued)

(58) Field of Classification Search
None
See application file for complete search history.

(56) References Cited

U.S. PATENT DOCUMENTS 3,899,328 A 8/1975 Limburg
3,957,725 A 5/1976 Limburg
(Continued)

FOREIGN PATENT DOCUMENTS

CN 1154102 A 7/1997
DE 44 22 332 A1 1/1996
(Continued)

OTHER PUBLICATIONS

Korean Office Action based on Korean Application No. 10-2009-7011190 dated Mar. 10, 2011.
(Continued)

*Primary Examiner* — J. L. Yang
(74) *Attorney, Agent, or Firm* — Cantor Colburn LLP

(57) ABSTRACT

The present invention provides a compound that can be readily purified and an organic EL device having a luminescent layer including the compound. In particular, the present invention provides a cyclic siloxane compound represented by Formula (1) below:

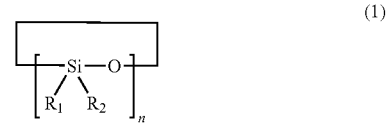

(1)

wherein, in Formula (1), $R_1$ and $R_2$ are each independently a luminescent monovalent group, a charge-transporting monovalent group, or another substituent; at least one of $R_1$ and $R_2$ is the charge-transporting monovalent group or the luminescent monovalent group; and n is an integer of 2 to 100, and an organic EL device having luminescent layer containing the compound.

14 Claims, 1 Drawing Sheet

(51) Int. Cl.
  *C07F 7/18* (2006.01)
  *C07F 7/21* (2006.01)
  *C09K 11/06* (2006.01)
  *H05B 33/14* (2006.01)
  *H01L 51/00* (2006.01)
  *H01L 51/50* (2006.01)

(52) U.S. Cl.
  CPC ...... *H05B 33/14* (2013.01); *C09K 2211/1014* (2013.01); *C09K 2211/1029* (2013.01); *C09K 2211/1033* (2013.01); *C09K 2211/1037* (2013.01); *C09K 2211/1044* (2013.01); *C09K 2211/1092* (2013.01); *C09K 2211/185* (2013.01); *H01L 51/008* (2013.01); *H01L 51/0059* (2013.01); *H01L 51/0085* (2013.01); *H01L 51/5012* (2013.01)

(56) References Cited

U.S. PATENT DOCUMENTS

| | | | |
|---|---|---|---|
| 6,066,426 | A | 5/2000 | Mott et al. |
| 6,140,004 | A | 10/2000 | Mott et al. |
| 6,184,322 | B1 | 2/2001 | Styring et al. |
| 6,485,847 | B1 | 11/2002 | Uchida et al. |
| 6,517,958 | B1 | 2/2003 | Sellinger et al. |
| 7,238,437 | B2 | 7/2007 | Igarashi et al. |
| 7,291,406 | B2 | 11/2007 | Thompson et al. |
| 8,004,177 | B2 | 8/2011 | Lee et al. |
| 2001/0019782 | A1* | 9/2001 | Igarashi ............. C07F 15/0033 428/690 |
| 2003/0148142 | A1* | 8/2003 | Fryd et al. .................. 428/690 |
| 2004/0067387 | A1* | 4/2004 | Kim et al. .................. 428/690 |
| 2004/0110031 | A1* | 6/2004 | Fukuda et al. ............. 428/690 |
| 2004/0258956 | A1* | 12/2004 | Matsusue .................. 428/690 |
| 2005/0238914 | A1* | 10/2005 | Lyu et al. .................. 428/690 |
| 2006/0134440 | A1 | 6/2006 | Crivello |
| 2006/0232201 | A1* | 10/2006 | Xu ............................. 313/506 |
| 2007/0112133 | A1* | 5/2007 | Lee et al. ................... 525/100 |
| 2007/0138483 | A1 | 6/2007 | Lee et al. |
| 2007/0155928 | A1 | 7/2007 | Koyama et al. |
| 2010/0052114 | A1* | 3/2010 | Hara et al. ................. 257/632 |

FOREIGN PATENT DOCUMENTS

| | | | |
|---|---|---|---|
| JP | 50-15899 | | 2/1975 |
| JP | 8-157575 | A | 6/1996 |
| JP | 2000-512984 | A | 10/2000 |
| JP | 2001-247859 | A | 9/2001 |
| JP | 2003-526876 | A | 9/2003 |
| JP | 2003-321546 | A | 11/2003 |
| JP | 2004-506050 | A | 2/2004 |
| JP | 2005-097589 | A | 4/2005 |
| JP | 2005100710 | A | 4/2005 |
| JP | 2005-314689 | A | 11/2005 |
| JP | 2006-124710 | A | 5/2006 |
| JP | 2007154184 | A | 6/2007 |
| JP | 2007-169593 | A | 7/2007 |
| KR | 2001-0031273 | A | 4/2001 |
| WO | 96/00208 | A1 | 1/1996 |
| WO | 00/22483 | A1 | 4/2000 |
| WO | 2005/019307 | A1 | 3/2005 |
| WO | WO 2005019307 | A1 * | 3/2005 ............. C08G 77/26 |
| WO | WO 2006/080205 | A1 * | 8/2006 ................ C07F 7/21 |

OTHER PUBLICATIONS

Chinese Office Action dated May 25, 2011 issued in corresponding Chinese Application No. 200780040661.5.
European Office Action dated Jul. 13, 2011 issued in corresponding European Application No. 07 830 987.9.
Maud, J.M. et al., "Carbazolylalkyl substituted cyclosiloxanes:synthesis and properties", Synthetic Metals, 1993, pp. 890-895, XP002628958.
John C. Mastrangelo; Design and Synthesis of Vitrifiable Low-Molar-Mass Organic Materials; thesis, University of Rochester, Rochester, NY (1996), pp. 8-9 and 17.
Sugiono et al.; Alkoxysilylation of π-systems with extended conjugation—reactive chromophores for organic-inorganic hybrid materials; Synthetic Metals 147 (2004); pp. 233-236.
Risse et al.; Di-and tetrafunctional initiators for the living ring-opening olefin metathesis polymerization of strained cyclic olefins; Macromolecules, 1989, vol. 22, pp. 3205-3210.
Farrell et al.; The preparation and catalytic hydroformylation activity of some halocarbonylrhodium (I) complexes containing phosphinoalkylorganosilicon ligands; Journal of Organometallic Chemistry, 1979, vol. 169, pp. 199-208.
Kim et al.; 2,2':6',2"-terpyridine and bis(2,2';6',2"-terpyridine) ruthenium (II) complex on the dendritic periphery; Journal of Organometallic Chemistry, 2003, vol. 673, pp. 77-83.

* cited by examiner

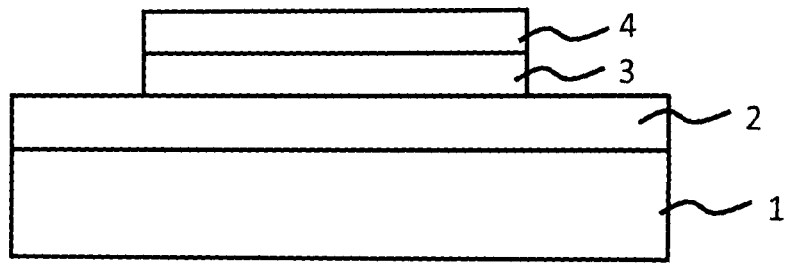

CYCLIC SILOXANE COMPOUND, ORGANIC ELECTROLUMINESCENCE DEVICE, AND USE OF THE SAME

TECHNICAL FIELD

The present invention relates to cyclic siloxane compounds, more specifically, cyclic siloxane compounds having a phosphorescent portion, organic electroluminescence devices using the cyclic siloxane compounds, and uses of the devices.

BACKGROUND ART

Since an organic electroluminescence device (in the Description, occasionally, referred to as organic EL device) emitting high-luminance light was reported in 1987 by C. W. Tang, et al. Eastman Kodak Co. (Appl. Phys. Lett., vol. 51, p. 913, 1987), development of materials for the organic EL device and improvement of device structure have rapidly progressed. Recently, practical application of the organic EL device to, for example, a car audio component or the display of a mobile phone has started. Currently, in order to further expand the use of the organic EL (electroluminescence), for example, development of material for improving luminous efficiency and durability and development of full-color display are being actively performed. In particular, in the application of the device to medium-sized panels, large-sized panels, or lightings, it is necessary to further increase luminance by improving luminous efficiency and to establish a method of mass production suitable for enlarging the size of a product.

Regarding a method of mass production of panels, vacuum deposition where a low molecular compound is evaporated under vacuum for forming a thin film on a substrate is conventionally used. However, this method has disadvantages such that: a vacuum facility is necessary, and a difficulty in forming an organic thin film having a uniform thickness increases with the size. Therefore, such a method is not necessarily suitable for mass-producing large-sized panels.

Meanwhile, as methods for readily increasing the size of a product, production processes using a luminescent high molecular weight material, that is, an ink-jetting method and a printing method, have been developed. In particular, the printing method can continuously form films with a large length and is therefore excellent in enlargement of the size of a product and mass productivity.

Recently, in order to expand the use of the organic EL device, material development using a phosphorescent compound having high luminous efficiency has been actively performed (for example, JP 2003-526876 A (Patent Document 1) and JP 2001-247859 A (Patent Document 2)).

Furthermore, JP 2005-314689 A (Patent Document 3) discloses a compound having a structure derived from a siloxane compound as a luminescent high molecular weight complex compound.

[Patent Document 1] JP 2003-526876 A
[Patent Document 2] JP 2001-247859 A
[Patent Document 3] JP 2005-314689 A

DISCLOSURE OF THE INVENTION

Problems to be Solved by the Invention

It is well known that an organic compound used for a luminescent layer is generally required to have a high purity in order to make an organic EL device emit light with high luminous efficiency.

However, though the high molecular weight complex compound described in Patent Document 3 can be applied to a large area by the ink-jetting method or the printing method, purification process of the high molecular weight compound is limited to, for example, reprecipitation purification, resulting in an insufficient purity of the compound. Thus, the high molecular weight complex compound is disadvantageous as a material for the luminescent layer of the organic EL device in the point of luminescent properties such as luminous efficiency. That is, in a usual purification of a high molecular weight compound, precipitation of a high molecular weight compound by adding a small amount of a good solvent solution dissolving the high molecular weight compound to a large amount of a poor solvent, so-called reprecipitation, is widely employed. However, this method is difficult to remove an impurity having a similar solubility in a solvent to that of a target high molecular weight compound. In addition, column chromatography is recently well employed as a method for simply purifying a low molecular weight compound, but when a high molecular weight compound is purified by the column chromatography using a common filler such as silica gel or alumina, the high molecular weight compound is tightly adsorbed to the filler and, thereby, cannot be purified.

The present invention has been made taking such problems into consideration, and it is an object thereof to provide a new compound having a structure derived from a siloxane compound, which is suitable as a material for a luminescent layer of an organic EL device, can be applied to a large area and can be purified to high purity by a simple purification process, and to provide an organic EL device including the compound in a luminescent layer, and a use of the device.

Means for Solving the Problems

The present inventors have conducted intensive studies and, as a result, found the fact that a compound having a cyclic siloxane skeleton can be readily purified compared to acyclic (linear) high molecular weight compounds having a conventional siloxane skeleton and can be increased in purity and exhibit high luminous efficiency when it is used as a material of the luminescent layer of an organic EL device, and thus the present invention has been achieved.

The present invention is summarized as follows:

[1]
A cyclic siloxane compound represented by Formula (1) below:

wherein, in Formula (1), $R_1$ and $R_2$ are each independently a luminescent monovalent group, a charge-transporting monovalent group, or another substituent; at least one of $R_1$ and $R_2$ is the charge-transporting monovalent group or the luminescent monovalent group; and n is an integer of 2 to 100;

[2]
The cyclic siloxane compound according to the above [1], wherein the charge-transporting monovalent group is a group obtained by substituting a hydrogen atom of a charge-transporting compound with a linking group X, and is linked to a Si atom in Formula (1) via the linking group X;

[3]

The cyclic siloxane compound according to the above [1] or [2], wherein the luminescent monovalent group is a group obtained by substituting a hydrogen atom of a luminescent compound with a linking group X, and is linked to a Si atom in Formula (1) via the linking group X;

[4]

The cyclic siloxane compound according to the above [2] or [3], wherein the linking group X is a single bond;

[5]

The cyclic siloxane compound according to the above [2] or [3], wherein the linking group X is a group represented by —(CH$_2$)$_n$—, wherein n is an integer of 1 to 20;

[6]

The cyclic siloxane compound according to the above [5], wherein the group represented by —(CH$_2$)$_n$—, wherein n is an integer of 1 to 20, is a group represented by —CH$_2$—CH$_2$—;

[7]

The cyclic siloxane compound according to any one of the above [1] to [6], wherein at least one of R$_1$ and R$_2$ in Formula (1) is a group obtained by substituting a hydrogen atom of a triarylamine derivative with a linking group X, and is linked to a Si atom in Formula (1) via the linking group X;

[8]

The cyclic siloxane compound according to any one of the above [1] to [7], wherein at least one of R$_1$ and R$_2$ in Formula (1) is a group obtained by substituting a hydrogen atom of a triarylborane derivative with a linking group X, and is linked to a Si atom in Formula (1) via the linking group X;

[9]

The cyclic siloxane compound according to any one of the above [1] to [8], wherein at least one of R$_1$ and R$_2$ in Formula (1) is a group obtained by substituting a hydrogen atom of a phosphorescent compound with a linking group X, and is linked to a Si atom in Formula (1) via the linking group X;

[10]

The cyclic siloxane compound according to the above [9], wherein the phosphorescent compound is an iridium complex;

[11]

A process of producing a cyclic siloxane compound represented by Formula (1) below:

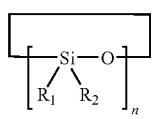

(1)

wherein, in Formula (1), R$_1$ and R$_2$ are each independently a luminescent monovalent group, a charge-transporting monovalent group, or another substituent; at least one of R$_1$ and R$_2$ is the charge-transporting monovalent group or the luminescent monovalent group; and n is an integer of 2 to 100), the said process comprising:

cyclocondensing monomers represented by Formula (10) below:

(10)

wherein, in Formula (10), R$_1$ and R$_2$ are each independently the same as R$_1$ and R$_2$ in Formula (1); and X$_1$ and X$_2$ are each independently a hydroxyl group, an alkoxy group, or a halogen atom;

[12]

A process of producing a cyclic siloxane compound represented by Formula (1) below:

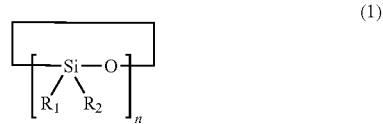

(1)

wherein, in Formula (1), R$_1$ and R$_2$ are each independently a luminescent monovalent group, a charge-transporting monovalent group, or another substituent; at least one of R$_1$ and R$_2$ is the charge-transporting monovalent group or the luminescent monovalent group; and n is an integer of 2 to 100, the said process comprising:

reacting a cyclic siloxane compound represented by Formula (20) below:

(20)

wherein, in Formula (20), R$_3$ is a hydrogen atom or the another substituent, and n is an integer of 2 to 100, with a charge-transporting compound having a vinyl group and capable of inducing the charge-transporting monovalent group and/or a luminescent compound having a vinyl group and capable of inducing the luminescent monovalent group;

[13]

A process of producing a cyclic siloxane compound represented by Formula (1) below:

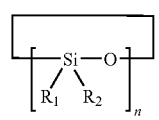

(1)

wherein, in Formula (1), R$_1$ and R$_2$ are each independently a luminescent monovalent group, a charge-transporting monovalent group, or another substituent; at least one of R$_1$ and R$_2$ is the charge-transporting monovalent group or the luminescent monovalent group; and n is an integer of 2 to 100, the said process comprising:

reacting a cyclic siloxane compound represented by Formula (30) below:

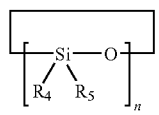
(30)

wherein, in Formula (30), $R_4$ and $R_5$ are each independently a substituent having a reactive group or the another substituent; at least one of $R_4$ and $R_5$ is the substituent having a reactive group; and n is an integer of 2 to 100, with a charge-transporting compound capable of inducing the charge-transporting monovalent group and/or a luminescent compound capable of inducing the luminescent monovalent group;

[14]

An organic electroluminescence device including a substrate, a pair of electrodes disposed on the substrate and, between the pair of electrodes, one or more organic layers having a luminescent layer, wherein the luminescent layer comprises the cyclic siloxane compound of any one of the above [1] to [10];

[15]

An image display apparatus including the organic electroluminescence device of the above [14]; and

[16]

An area light source including the organic electroluminescence device of the above [14].

Advantages of the Invention

The purity of the cyclic siloxane compound according to the present invention can be increased by a simple process, and the organic EL device using the compound in the luminescent layer has high luminous efficiency.

BRIEF DESCRIPTION OF DRAWINGS

The FIGURE is a cross-sectional view of an organic EL device according to an embodiment of the present invention.

REFERENCE NUMERALS 1 glass substrate
2 anode
3 luminescent layer
4 cathode

BEST MODES FOR CARRYING OUT THE INVENTION

The present invention will be specifically described below.

Cyclic Siloxane Compound

The cyclic siloxane compound of the present invention is represented by Formula (1) below:

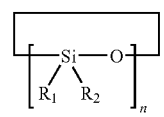
(1)

wherein, in Formula (1), $R_1$ and $R_2$ are each independently a charge-transporting monovalent group, a luminescent monovalent group, or another substituent; at least one of $R_1$ and $R_2$ is the charge-transporting monovalent group or the luminescent monovalent group; and n is an integer of 2 to 100.

The cyclic siloxane compound of the present invention has repeating units:

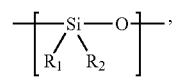

which may be the same or different from each other. Therefore, the cyclic siloxane compound of the present invention may comprise, for example, repeating units having a hole-transporting monovalent group and repeating units having a luminescent monovalent group.

Since acyclic (linear) siloxane compounds having the same side chains as those of the cyclic siloxane compound of the present invention are tightly adsorbed to the filler, such as silica gel or alumina, of column chromatography, they cannot be purified by column chromatography. On the other hand, since the strength of adsorption of the cyclic siloxane compound of the present invention to the filler is proper, the compound can be purified by column chromatography, and, therefore, the purity thereof can be readily increased.

Furthermore, the cyclic siloxane compound of the present invention can be applied to a substrate by ink jetting, spin coating, dip coating, printing or the like for forming a film and is therefore suitable for producing a large-sized device and mass production.

In Formula (1), n is an integer of 2 to 100, preferably 2 to 30, more preferably 2 to 10, and most preferably 3 to 5. When n is too large than this range, it is difficult to synthesize the above-mentioned cyclic siloxane compound, and it is also difficult to find out a difference in advantageous effects between such a cyclic siloxane compound and the linear siloxane compounds.

In Formula (1), $R_1$ and $R_2$ are each independently a luminescent monovalent group, a charge-transporting monovalent group, or another substituent. Examples of these groups are as follows:

Luminescent Monovalent Group

The luminescent monovalent group is a group obtained by substituting a hydrogen atom of a luminescent compound with a linking group X. This linking group X links a Si atom in the cyclic siloxane compound of the present invention and the luminescent compound. Examples of the linking group X include a single bond, —O—, —S—, —SO—, —SO$_2$—, and divalent organic groups having 1 to 20 carbon atoms and optionally having a hetero atom. Preferred are a single bond and —(CH$_2$)$_n$— (n is 1 to 20), and further preferred are a single bond and —CH$_2$—CH$_2$—.

The luminescent compound may be a fluorescent compound or a phosphorescent compound, but the phosphorescent compound is preferred because of its high luminous efficiency. The phosphorescent compound is a metal complex having a metal element selected from iridium, platinum, and gold. In particular, the iridium complex has high luminous efficiency and is therefore preferred. Examples of the phosphorescent compounds include metal complexes represented by Formulae (E-1) to (E-49).

E-1
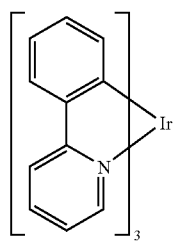
E-2
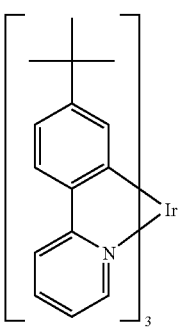
E-3
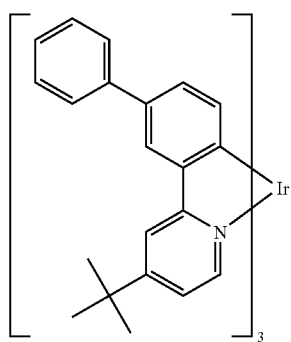
E-4
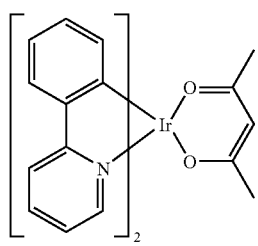
E-5
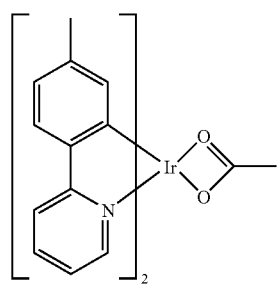
E-6
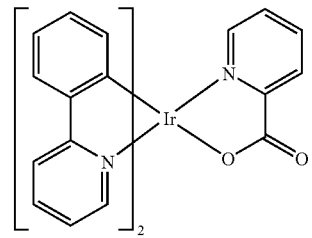
E-7
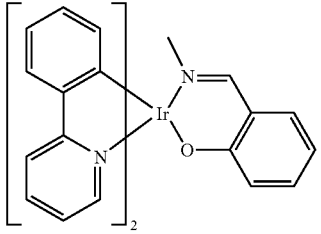
E-8
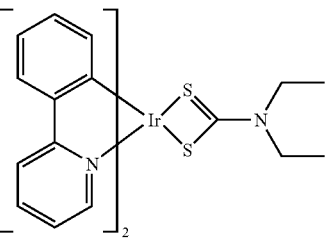
E-9
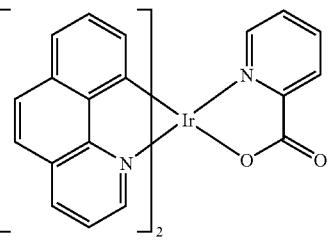
E-10
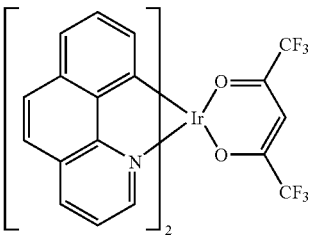
E-11
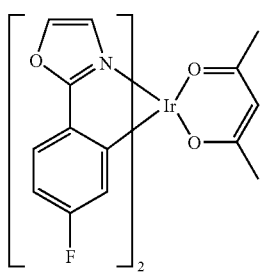

E-12
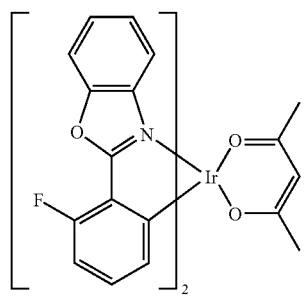
E-13
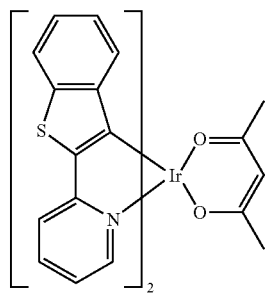
E-14
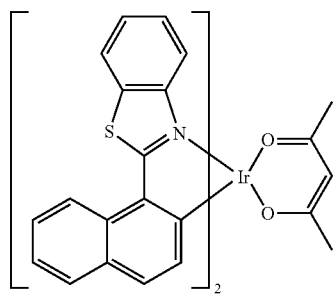
E-15
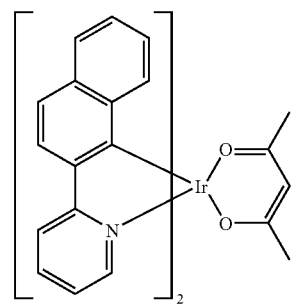
E-16
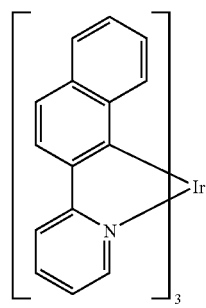
E-17
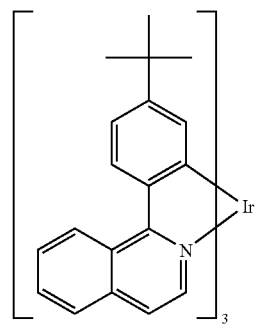
E-18
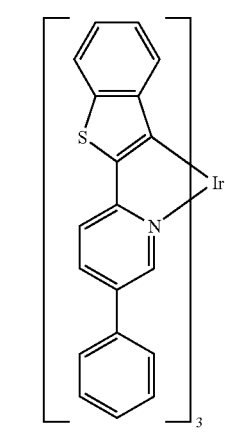
E-19
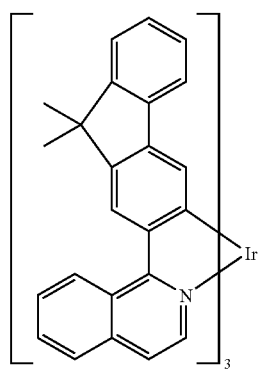
E-20
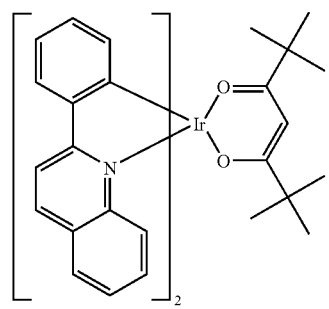

E-21
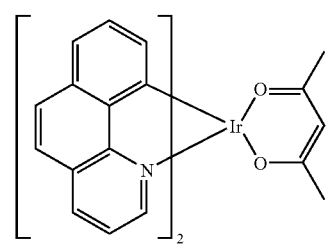
E-22
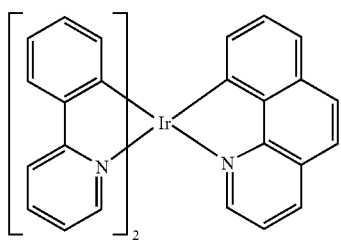
E-23
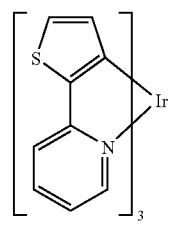
E-24
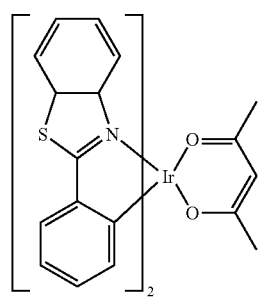
E-25
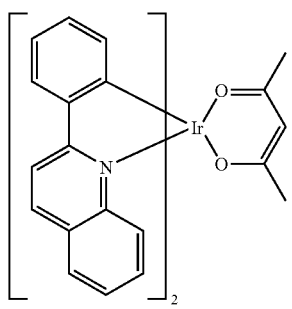
E-26
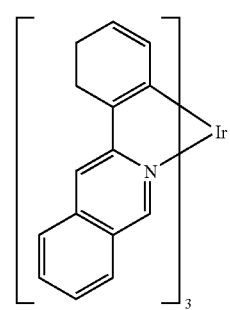
E-27
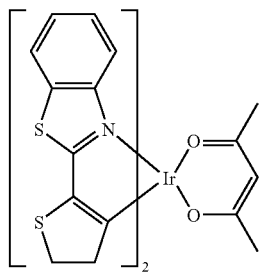
E-28
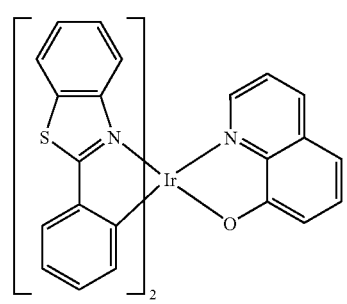
E-29
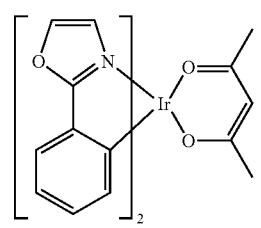
E-30
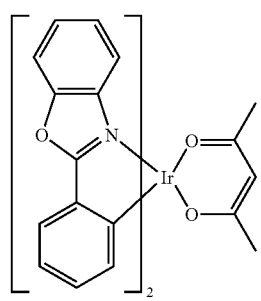
E-31
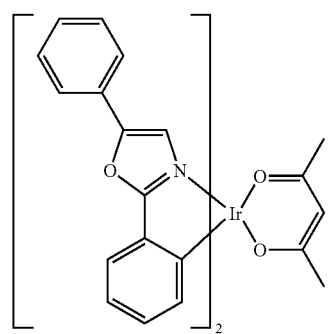

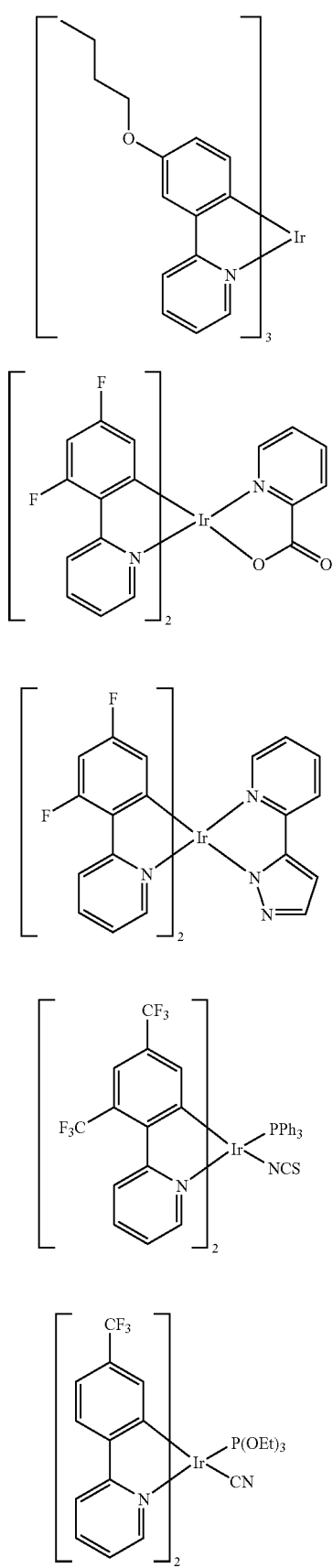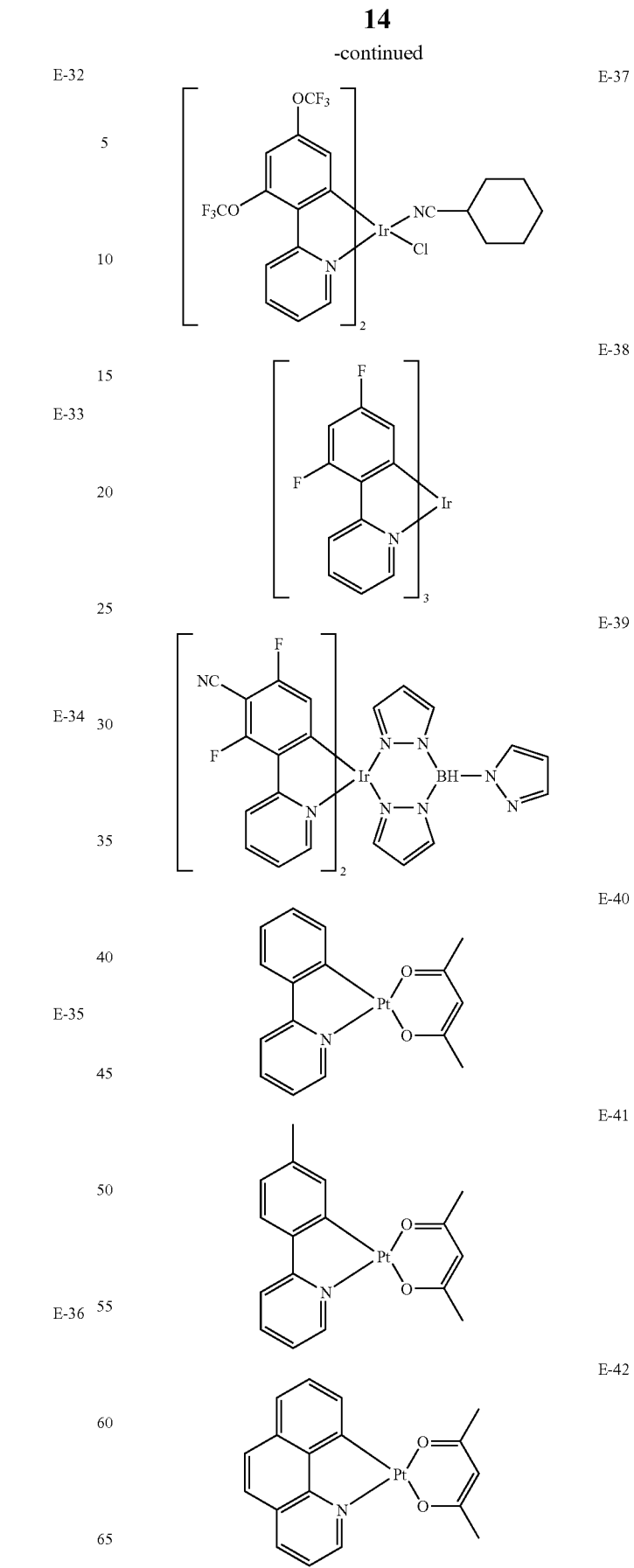

E-43 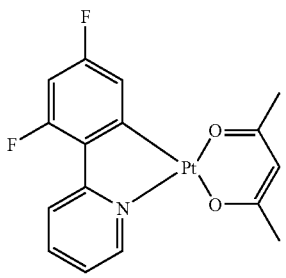

E-44 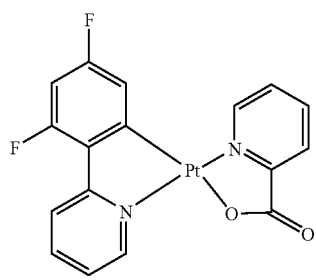

E-45 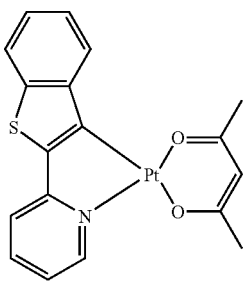

E-46 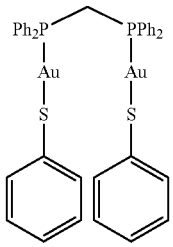

E-47 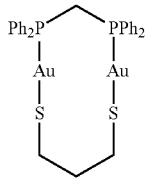

E-48 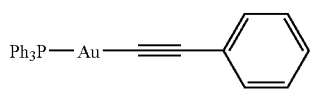

E-49 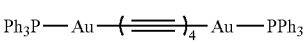

In Formulae (E-35) and (E-46) to (E-49), Ph denotes a phenyl group.

Charge-Transporting Monovalent Group

The charge-transporting monovalent group is a group obtained by substituting a hydrogen atom of an organic compound having either one or both hole-transporting and electron-transporting functions (hereinafter, occasionally referred to as "charge-transporting compound") with the linking group X. This linking group X links a Si atom in the cyclic siloxane compound of the present invention and the charge-transporting compound. Examples of the linking group X include a single bond, —O—, —S—, —SO—, —SO$_2$—, and divalent organic groups having 1 to 20 carbon atoms and optionally having a hetero atom. Preferred are a single bond and —(CH)$_2$— (n is 1 to 20), and more preferred are a single bond and —CH$_2$—CH$_2$—. Examples of the charge-transporting compound include compounds represented by Formulae (E-50) to (E-67).

E-50 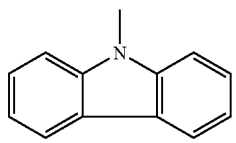

E-51 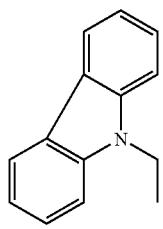

E-52 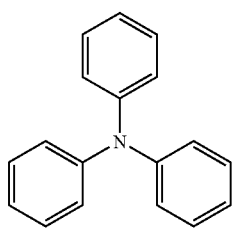

E-53 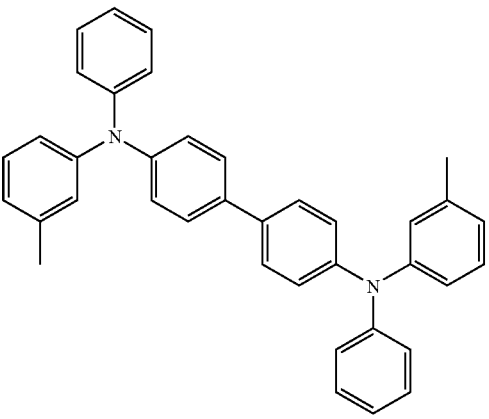

E-54
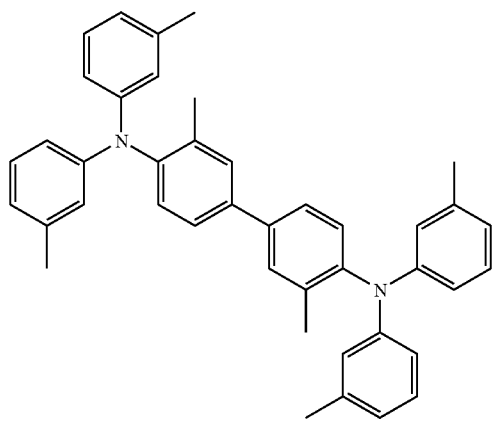
E-55
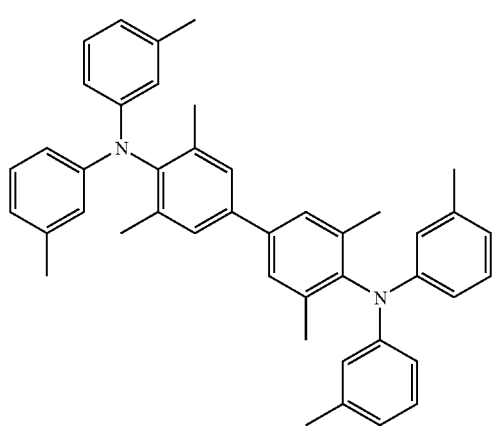
E-56
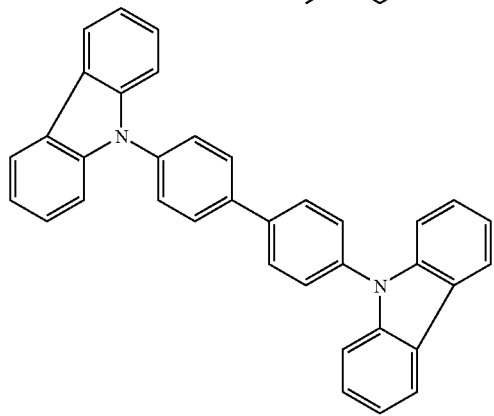
E-57
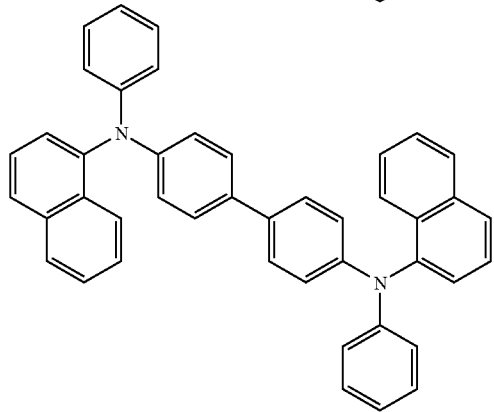
E-58
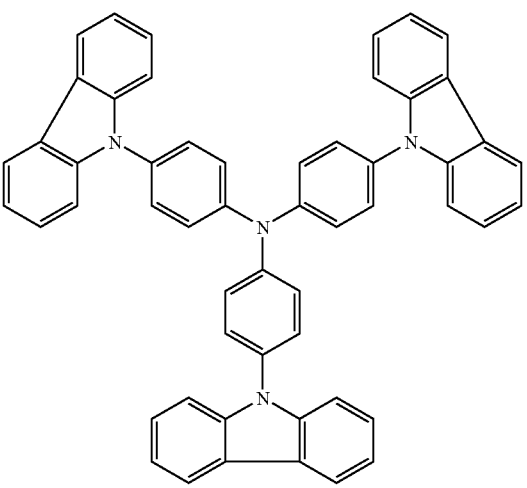
E-59
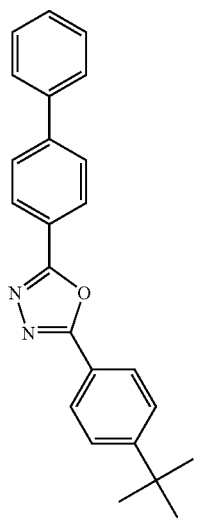
E-60
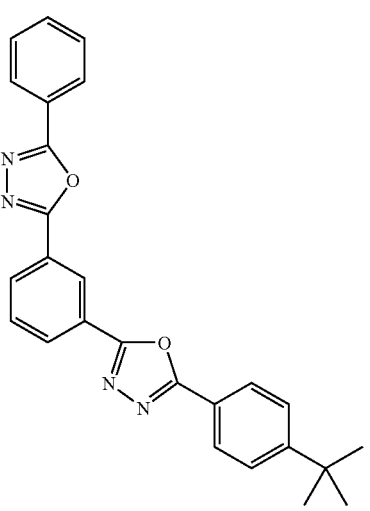

-continued

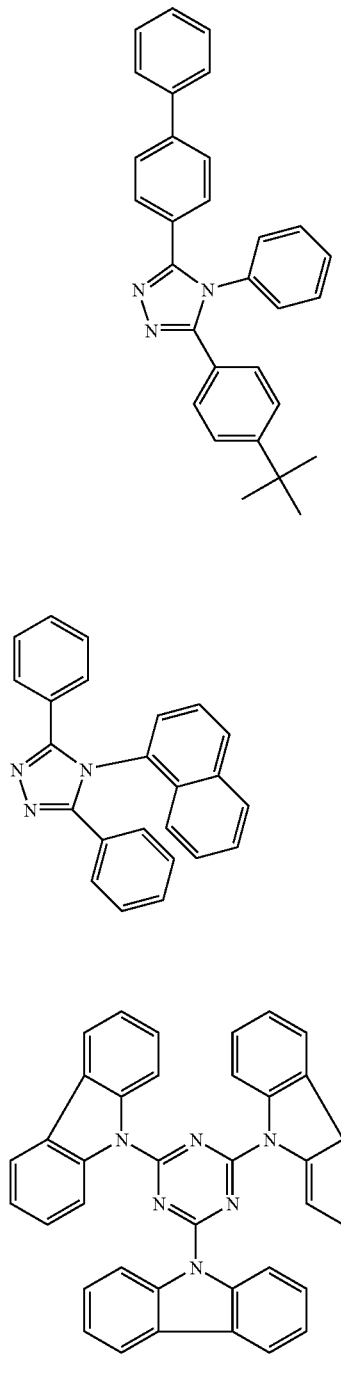

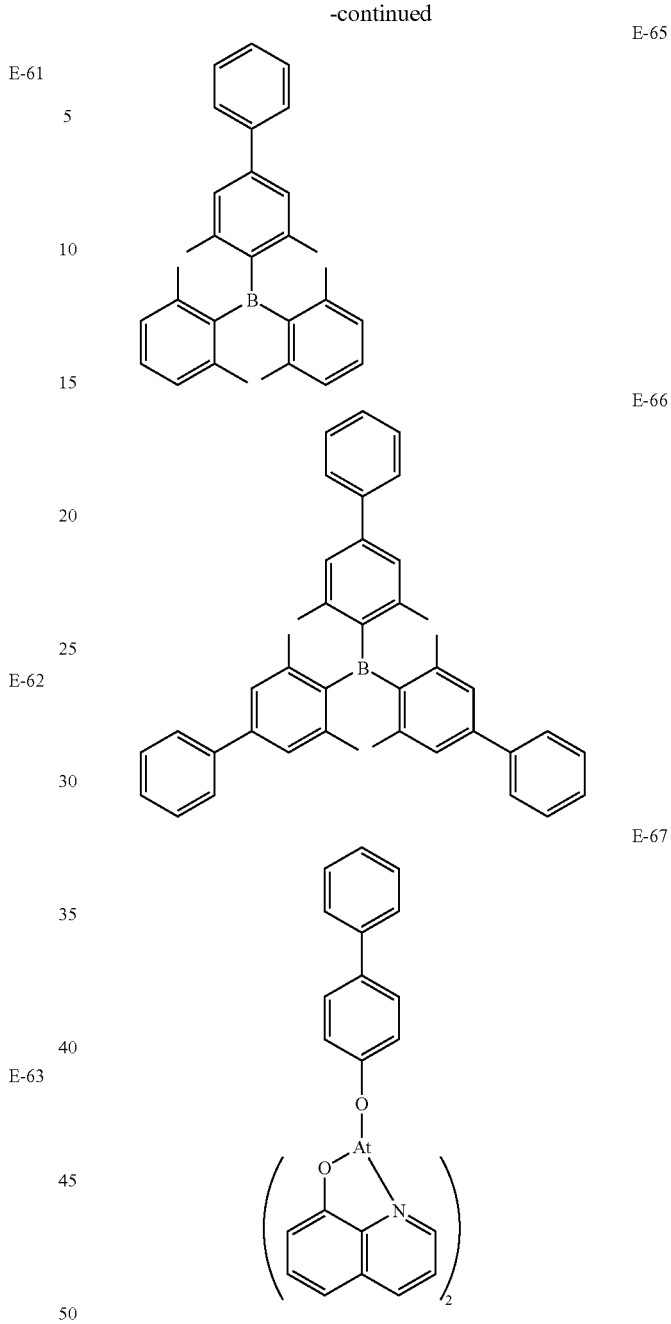

Another Substituent

Examples of the another substituent include aryl groups having 6 to 60 carbon atoms, monovalent heterocyclic groups, monovalent aromatic amine groups having 6 to 60 carbon atoms, alkyl groups having 1 to 20 carbon atoms, a hydroxyl group, alkoxy groups having 1 to 20 carbon atoms, aryloxy groups having 6 to 60 carbon atoms, arylalkyl groups having 7 to 60 carbon atoms, arylalkoxy groups having 7 to 60 carbon atoms, aryloxyalkyl groups having 7 to 60 carbon atoms, aryloxyalkoxy groups having 7 to 60 carbon atoms, arylamino groups having 6 to 60 carbon atoms, substituted silyloxy groups, a hydrogen atom, halogen atoms, a carboxyl group, alkyloxycarbonyl groups having 2 to 20 carbon atoms, alkylcarbonyloxy groups having 2 to 20 carbon atoms, an amino group, and alkylamino groups having 1 to 20 carbon atoms.

Production Process

Next, the process of producing the cyclic siloxane compound of the present invention will be described by the following three examples of the process, but the process of producing the cyclic siloxane compound of the present invention is not limited thereto.

A first example of the process is a method of producing the cyclic siloxane compound of the present invention comprising cyclocondensing monomers represented by Formula (10) below in the presence of a suitable catalyst and water,

wherein, in Formula (10), $R_1$ and $R_2$ are each independently the same as $R_1$ and $R_2$ in Formula (1), i.e., a luminescent monovalent group, a charge-transporting monovalent group, or another substituent; at least one of $R_1$ and $R_2$ is the luminescent monovalent group or the charge-transporting monovalent group; and $X_1$ and $X_2$ are each independently a hydroxyl group, an alkoxy group, or a halogen atom.

The catalyst used herein may be an acidic catalyst or an alkaline catalyst, but an alkaline catalyst is preferred from the viewpoint of selectivity of products. Examples of the acidic catalyst include hydrochloric acid, sulfuric acid, acetic acid, and formic acid. Examples of the alkaline catalyst include sodium hydroxide, potassium hydroxide, sodium carbonate, potassium carbonate, rubidium carbonate, cesium carbonate, sodium methoxide, sodium ethoxide, potassium-tert-butoxide, n-butylamine, triethylamine, p-dimethylaminoethanol, diethylamine, ethylenediamine, tetramethylammonium hydroxide, and tetraethylammonium hydroxide. In order to more selectively perform a reaction, it is possible to perform the reaction in the presence of an acid catalyst once and then further perform the reaction after addition of an excess amount of an alkaline catalyst.

The reaction temperature is usually 20 to 100° C., and the reaction time is 1 to 1000 hours. Since this cyclocondensation reaction is an equilibrium reaction, a longer reaction time is preferred. However, an excessively long reaction time is disadvantageous from the viewpoint of production efficiency. An excessively short reaction time decreases the yield.

The monomer represented by Formula (10) can be produced by, for example, hydrosilylation of a compound having a vinyl group and a silane compound in the presence of a suitable catalyst. As the compounds having a vinyl group, conventionally known charge-transporting vinyl compounds and luminescent vinyl compounds can be used, and examples of such compounds include the vinyl compound described in Japanese JP 2005-097589 A. Examples of the silane compound include dihydroxysilane, dimethoxymethylsilane, diethoxymethylsilane, dimethoxyphenylsilane, dimethoxysilane, dichloromethylsilane, dichlorophenylsilane, and dichlorosilane. Examples of the catalyst include hexachloroplatinic(IV) acid hexahydrate, dichloro (1,5-cyclooctadiene)platinum(II), and platinum(0)-1,3-divinyl-1,1,3,3-tetramethyldisiloxane complex.

The monomer represented by Formula (10) can also be produced by reacting an aryllithium compound or a Grignard reagent with a silane compound. The aryllithium compound and the Grignard reagent can be synthesized from the corresponding halogenated compounds according to an ordinary method. Examples of the silane compound include dimethoxymethylchlorosilane, trimethoxymethylsilane, triethoxymethylsilane, trimethoxyphenylsilane, and tetraethoxysilane.

Furthermore, the monomer represented by Formula (10) can be produced by reacting a silane compound having a reactive group with a compound that can react with the reactive group to form a bond (for example, an ether bond, an ester bond, an amide bond, a C—C bond, or a C=C bond) with the silane compound.

A second example of the process is a method of producing the cyclic siloxane compound of the present invention comprising reacting a cyclic siloxane compound represented by Formula (20) with a charge-transporting compound capable of inducing a charge-transporting monovalent group and having a vinyl group and/or a luminescent compound capable of inducing a luminescent monovalent group and having a vinyl group to produce the cyclic siloxane compound.

In Formula (20), $R_3$ is a hydrogen atom or another substituent, and n is an integer of 2 to 100, preferably 2 to 30, and more preferably 2 to 10.

The another substituent is the same as the "another substituent" in Formula (1) described above.

The cyclic siloxane compound of the present invention can be produced by hydrosilylation of a compound represented by Formula (20) with a charge-transporting compound capable of inducing a charge-transporting monovalent group and having a vinyl group and/or a luminescent compound capable of inducing a luminescent monovalent group and having a vinyl group in the presence of a suitable catalyst.

The "charge-transporting monovalent group" is the same as the "charge-transporting monovalent group" in Formula (1) described above, and the "luminescent monovalent group" is the same as the "luminescent monovalent group" in Formula (1) described above.

Examples of the compound represented by Formula (20) include methylhydrocyclosiloxane, ethylhydrocyclosiloxane, phenylhydrocyclosiloxane, and dihydrocyclosiloxane. As the charge-transporting compound and/or luminescent compound having a vinyl group, conventionally known compounds can be used, and, for example, the vinyl compound described in Japanese Unexamined Patent Application Publication No. 2005-097589 can be used. Examples of the catalyst include hexachloroplatinic(IV) acid hexahydrate, dichloro(1,5-cyclooctadiene)platinum(II), and platinum(0)-1,3-divinyl-1,1,3,3-tetramethyldisiloxane complex.

A third example of the process is a method of producing the cyclic siloxane compound of the present invention comprising reacting a cyclic siloxane compound represented by Formula (30) with a charge-transporting compound capable of inducing a charge-transporting monovalent group and/or a luminescent compound capable of inducing a luminescent monovalent group to produce the cyclic siloxane compound.

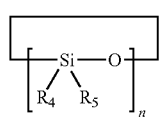

(30)

In Formula (30), $R_4$ and $R_5$ are each independently a substituent having a reactive group or another substituent, and at least one of $R_4$ and $R_5$ is a reactive substituent.

n is an integer of 2 to 100, preferably 2 to 30, and more preferably 2 to 10.

The cyclic siloxane compound of the present invention can be produced by reacting a compound represented by Formula (30) with a charge-transporting compound and/or a luminescent compound that can react with the reactive group of the compound represented by Formula (30) to form a bond with the compound. Examples of the reactive group in Formula (30) include a hydroxyl group, a carboxyl group, an aldehyde group, an acetal group, a ketone group, an amino group, an ester group, an amide group, a carbonate group, a vinyl group, an ethynyl group, and a mercapto group, but the reactive group is not limited thereto.

Examples of the "substituent having a reactive group" include hydroxyalkyl groups such as a hydroxymethyl group and a hydroxyethyl group; carboxyalkyl groups such as a carboxymethyl group and a carboxyethyl group; formylalkyl groups such as a formylmethyl group; a dimethoxymethyl group; a 2,2-dimethoxyethyl group; aminoalkyl groups such as an aminoethyl group and a 3-aminopropyl group; vinylalkyl groups; ethynylalkyl groups; and mercaptoalkyl groups, but the substituent are not limited thereto.

The "another substituent" is the same as the "another substituent" in Formula (1).

The "charge-transporting compound and/or luminescent compound" is a compound obtained by substituting a hydrogen atom of the above-described charge-transporting compound and/or luminescent compound with a substituent having a group that can react with the reactive group in Formula (30) to form a bond. The "charge-transporting monovalent group" is the same as the charge-transporting monovalent group" in Formula (1) described above, and the "luminescent monovalent group" is the same as the "luminescent monovalent group" in Formula (1) described above.

The group that can react with the reactive group in Formula (30) to form a bond is, for example, an isocyanato group, a carboxyl group, an acid chloride (R—COCl), or a halogenated alkyl group when the reactive group in Formula (30) is a hydroxy group, an amino group, or a mercapto group; and a hydroxyl group, an amino group, or an acyloxy group when the reactive group in Formula (30) is a carboxyl group.

Organic EL Device

Organic Layer having Luminescent Layer

The organic EL device according to the present invention is an organic electroluminescence device including a substrate, a pair of electrodes disposed on the substrate and, between the pair of electrodes, one or more organic layers having a luminescent layer, wherein the luminescent layer comprises the cyclic siloxane compound represented by Formula (1).

When the cyclic siloxane compound does not have a luminescent monovalent group, the luminescent layer comprises the cyclic siloxane compound represented by Formula (1) and a luminescent compound. This luminescent compound may be a conventionally known luminescent compound.

The FIGURE shows an example of the structure of the organic EL device according to the present invention, but the structure of the organic EL device according to the present invention is not limited thereto. In the FIGURE, a luminescent layer (3) is disposed between an anode (2) and a cathode (4) disposed on a transparent substrate (1). The organic EL device may have a hole-injection layer between the anode (2) and the luminescent layer (3) or may have an electron-injection between the luminescent layer (3) and the cathode (4).

The process of producing the organic layer is not particularly limited. For example, the organic layer can be formed as follows: First, (A) a solution dissolving the cyclic siloxane compound represented by Formula (1) is prepared. The solvent used for the preparation of the solution is not particularly limited, and examples thereof include chlorinated solvents such as chloroform, methylene chloride, and dichloroethane, ether solvents such as tetrahydrofuran and anisole, aromatic hydrocarbon solvents such as toluene and xylene, ketone solvents such as acetone and methylethylketone, and ester solvents such as ethyl acetate, butyl acetate, and ethyl cellosolve acetate. Then, the thus prepared solution is applied to a substrate for forming a film by, for example, ink jetting, spin coating, dip coating, or printing. The concentration of the solution is determined depending on the compound used and film-forming conditions. For example, in the case of spin coating or dip coating, the concentration is preferably 0.1 to 10 wt %. Since the organic layer can be thus readily formed, simplification of the manufacturing process can be realized, and also large sized devices can be formed.

Other Raw Materials

Each layer described above may be formed by a mixture containing a polymer material as a binder. Examples of the polymer material include polymethylmethacrylates, polycarbonates, polyesters, polysulfones, and polyphenylene oxides.

Furthermore, the material of each layer described above may be a mixture of materials having a different function from each other. For example, each layer may be formed by a mixture of a luminescent material, a hole-transporting material, or an electron-transporting material. The organic layer comprising the cyclic siloxane compound of the invention may further comprise another hole-transporting material and/or electron-transporting material for ensuring the charge-transporting property. This transporting material may be a low molecular weight compound or may be a high molecular weight compound.

Examples of the hole-transporting material for forming the hole-transporting layer or the hole-transporting material contained in the luminescent layer include TPD (N,N'-dimethyl-N,N'-(3-methylphenyl)-1,1'-biphenyl-4,4'-diamine); α-NPD (4,4'-bis[N-(1-naphthyl)-N-phenylamino]biphenyl); low molecular weight triphenylamine derivatives such as m-MTDATA (4,4',4''-tris(3-methylphenylphenylamino)triphenylamine); polyvinylcarbazole; high molecular weight compounds obtained by introducing polymerizable substituents into the above-mentioned triphenylamine derivatives followed by polymerizing; and fluorescent high molecular weight compounds such as polyparaphenylenevinylene and polydialkylfluorene. Examples of the high molecular weight compounds include the high molecular weight compounds having a triphenylamine skeleton disclosed in JP 8-157575 A. The hole-transporting material may be used alone or as a mixture of two or more kinds. Different kinds of the hole-transporting materials may be used so as to be laminated. Since the thickness of the hole-transporting layer depends on, for example, electric conductivity of the hole-transporting layer, it cannot be categorically determined, but is preferably 1 nm to 5 µm, more preferably 5 nm to 1 µm, and most preferably 10 to 500 nm.

Examples of the electron-transporting material for forming the electron-transporting layer or the electron-transporting material mixed in the luminescent layer include low molecular weight compounds quinolinol derivative metal complexes such as Alq3 (aluminum tris(quinolinolate)), oxadiazole derivatives, triazole derivatives, imidazole derivatives, triazine derivatives, and triarylborane derivatives; and high molecular weight compounds obtained by introducing polymerizable substituents into the above-mentioned low molecular compounds followed by polymerizing. Examples of the high molecular weight compounds include poly-PBD disclosed in JP 10-1665 A. The electron-transporting material may be used alone or as a mixture of two or more kinds. Different kinds of the electron-transporting materials may be used so as to be laminated. Since the thickness of the electron-transporting layer depends on, for example, electric conductivity of the electron-transporting layer, it cannot be categorically determined, but is preferably 1 nm to 5 µm, more preferably 5 nm to 1 µm, and most preferably 10 to 500 nm.

Furthermore, a hole-blocking layer may be disposed adjacent to the luminescent layer on the cathode side in order to prevent holes from passing through the luminescent layer and to efficiently recombine holes and electrons in the luminescent layer. In order to form the hole-blocking layer, a known material such as a triazole derivative, an oxadiazole derivative, or a phenanthroline derivative is used.

A hole-injection layer may be disposed between the anode and the luminescent layer in order to reduce the injection barrier in injection of holes. In order to form the hole-injection layer, a known material such as copper phthalocyanine, a mixture of polyethylenedioxythiophene (PEDOT) and polystyrene sulfonate (PSS), or a fluorocarbon is used.

An insulation layer having a thickness of 0.1 to 10 nm may be disposed, in order to improve the electron injection efficiency, between the cathode and the electron-transporting layer or between the cathode and the organic layer laminated so as to be adjacent to the cathode. In order to form the insulation layer, a known material such as lithium fluoride, magnesium fluoride, magnesium oxide, or alumina is used.

The material used for the anode may be a known transparent electroconductive material, for example, ITO (indium tin oxide), tin oxide, zinc oxide, or an electroconductive polymer such as polythiophene, polypyrrole, and poylaniline. The electrode formed of this transparent electroconductive material preferably has a surface resistance of 1 to 50Ω/□ (ohm/square). The thickness of the anode is preferably 50 to 300 nm.

The material used for the cathode may be a known cathode material, for example, an alkali metal such as Li, Na, K, and Cs; an alkaline earth metal such as Mg, Ca, and Ba; Al; a MgAg alloy; and an alloy of Al and an alkali metal or an alkaline earth metal, such as AlLi and AlCa. The thickness of the cathode is preferably 10 nm to 1 µm and more preferably 50 to 500 nm. When a metal having high activity, such as alkali metals and alkaline earth metals, is used as the cathode, the thickness of the cathode is preferably 0.1 to 100 nm and more preferably 0.5 to 50 nm. In such a case, in order to protect the cathode metal, a metal layer that is stable to the atmosphere is laminated on the cathode. Examples of the metal for forming this metal layer include Al, Ag, Au, Pt, Cu, Ni, and Cr. The thickness of the metal layer is preferably 10 nm to 1 µm and more preferably 50 to 500 nm.

The substrate used in the organic EL device according to the present invention is an insulation substrate having transparency to the luminous wavelength of the above-mentioned luminescent material. Examples of the substrate include transparent plastic such as PET (polyethylene terephthalate) and polycarbonate, in addition to glass.

The hole-transporting layer, the luminescent layer, and the electron-transporting layer are formed by, for example, resistance heating deposition, electron-beam deposition, sputtering, ink jetting, spin coating, printing, spraying, or dispensing. In the case of a low molecular weight compound, the resistance heating deposition or the electron-beam deposition is preferably carried out. In the case of a high molecular weight compound, ink jetting, spin coating, or printing is preferably carried out.

The film of the anode is formed by, for example, electron-beam deposition, sputtering, chemical reaction, or coating of an anode material. The film of the cathode is formed by, for example, resistance heating deposition, electron-beam deposition, sputtering, or ion-plating of a cathode material.

Use

The organic EL device according to the present invention is preferably applied to image displays as a pixel by a matrix system or a segment system by known methods. Furthermore, the organic EL device is also preferably used as an area light source without forming a pixel.

Specifically, the organic EL device according to the present invention is preferably used, for example, in displays of a computer, a TV, a mobile phone terminal, a mobile phone, a car navigation system, the viewfinder of a video camera, and so on, and backlights, electronic photographs, illumination light sources, recording light sources, exposure light sources, reading light sources, labels, signs, interiors, and optical communications.

EXAMPLES

The present invention will be further specifically described based on Examples below, but the present invention is not limited these Examples.
Measurement Apparatus and Others
1) $^1$H-NMR
  Apparatus: Japan Electron Optics Laboratory (JEOL), JNM EX270, 270 Mz
  Solvent: deuterated chloroform
2) Gel Permeation Chromatography (GPC)
  Apparatus: Showa Denko K.K., Shodex GPC-101
  Column: Shodex KF–G+LF804×3
  Eluent: tetrahydrofuran (THF)
  Flow rate: 1 mL/min
  Column temperature: 40° C.
3) MALDI-TOF-MS (Matrix-Assisted Laser Desorption/Ionization-Time of Flight Mass Spectrometry)
  Apparatus: BRUKER Co., DALTONICS autoflex
  Laser light source: $N_2$ laser (wavelength: 337 nm)
  Measurement mode: reflector mode, positive ion mode
  Measurement mass range (m/z): 500 to 10000
  Cumulated number: 1000
  Matrix: dithranol (THF solution)

Example 1

Synthesis of Cyclic Siloxane Compound (1)

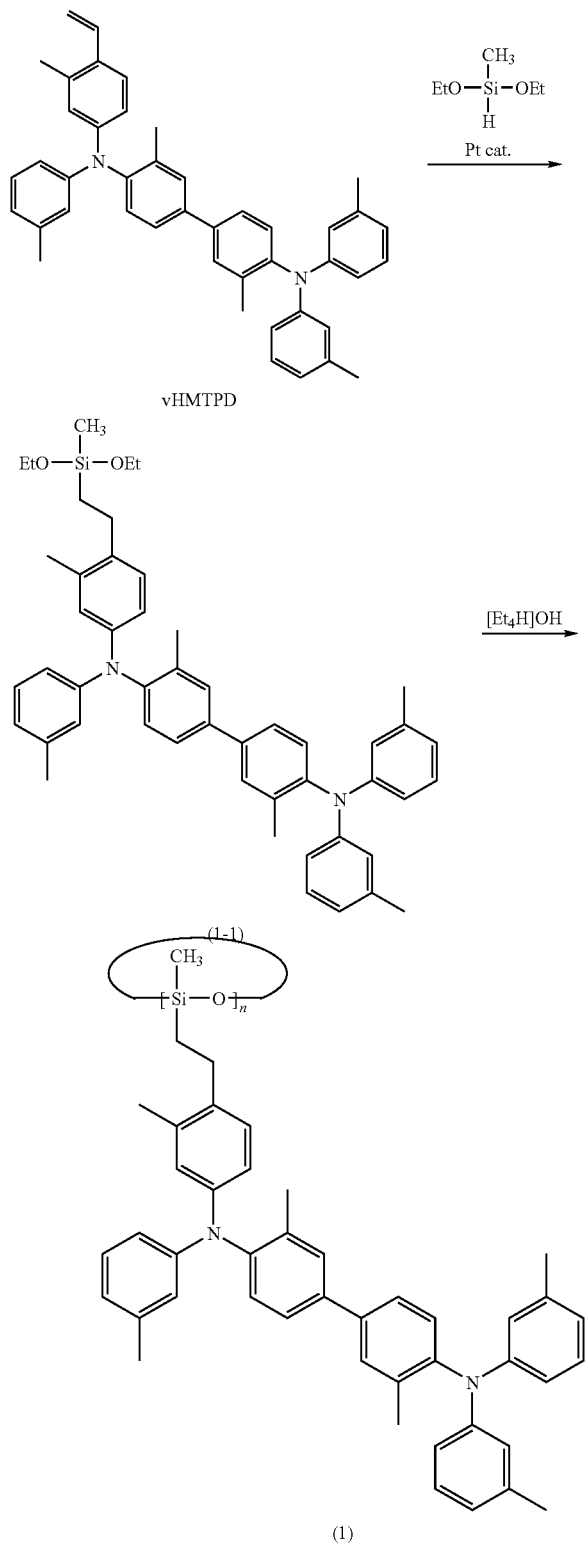

Description will be given with reference to the above-mentioned scheme.

Synthesis of Compound (1-1)

1.796 g of vHMTPD was put in a three-necked recovery flask. After the replacement of inside of the recovery flask with nitrogen, 15 mL of anhydrous toluene was added to the flask to dissolve the vHMTPD. To this toluene solution was added 959 μL of diethoxymethylsilane and 381 mg of a xylene solution containing 3% platinum(0)-1,3-divinyl-1,1,3,3-tetramethyldisiloxane complex (Aldrich reagent). The resulting mixture was stirred at room temperature for 1 hour for reaction. After the reaction, the solvent was evaporated and the residue was purified by silica gel column chromatography (eluent: chloroform/hexane=gradient from 1/3 to 3/1). The eluent was evaporated, and the residue was dissolved in a small amount of acetone and was dropwise added to a large amount of methanol for precipitation. The resulting precipitate was collected by filtration and was vacuum-dried to give a compound (1-1) as a white powder.

The amount of the compound was 1.404 g, and the yield was 66%. Identification was performed by $^1$H-NMR.

$^1$H-NMR (270 MHz, CDCl$_3$) ppm: 7.49-7.42 (m, 4H, ArH), 7.17-7.00 (m, 6H, ArH), 6.82-6.70 (m, 11H, ArH), 3.53 (s, 6H, —OCH$_3$), 2.62 (m, 2H, —CH$_2$—), 2.25-2.20 (m, 12H, —CH$_3$), 2.08 (s, 6H, —CH$_3$), 0.94 (m, 2H, —CH$_2$—), 0.13 (s, 3H, SiCH$_3$).

Synthesis of Compound (1)

100 mg of the compound (1-1) was put in a three-necked recovery flask. After the replacement of inside of the recovery flask with nitrogen, 1.5 mL of anhydrous THF was added to the flask to dissolve the compound (1-1). To this THF solution was added 50 mg of an aqueous solution containing 20% tetraethylammonium hydroxide. The resulting mixture was stirred at room temperature for 24 hours for reaction. After the reaction, one drop of acetic acid was added to the reaction solution for neutralization. The solvent was evaporated and the residue was purified by silica gel chromatography (eluent: chloroform/hexane=1/3). The solvent was evaporated, and the residue was dissolved in a small amount of acetone and was dropwise added to a large amount of methanol for precipitation. The resulting precipitate was collected by filtration and was vacuum-dried to give a compound (1) as a white powder.

The amount of the compound was 85 mg, and the yield was 95%. Identification was performed by $^1$H-NMR and MALDI-TOF-MS. The MALDI-TOF-MS confirmed that the main component of the compound (1) was a cyclic tetramer (n=4).

$^1$H-NMR (270 MHz, CDCl$_3$) ppm: 7.50-7.35 (m, 4H, ArH), 7.16-6.96 (m, 6H, ArH), 6.82-6.65 (m, 11H, ArH), 2.63 (m, 2H, —CH$_2$—), 2.24-2.04 (m, 18H, —CH$_3$), 0.89 (m, 2H, —CH$_2$—), 0.16 (m, 3H, SiCH$_3$).

Example 2

Synthesis of Cyclic Siloxane Compound (2)

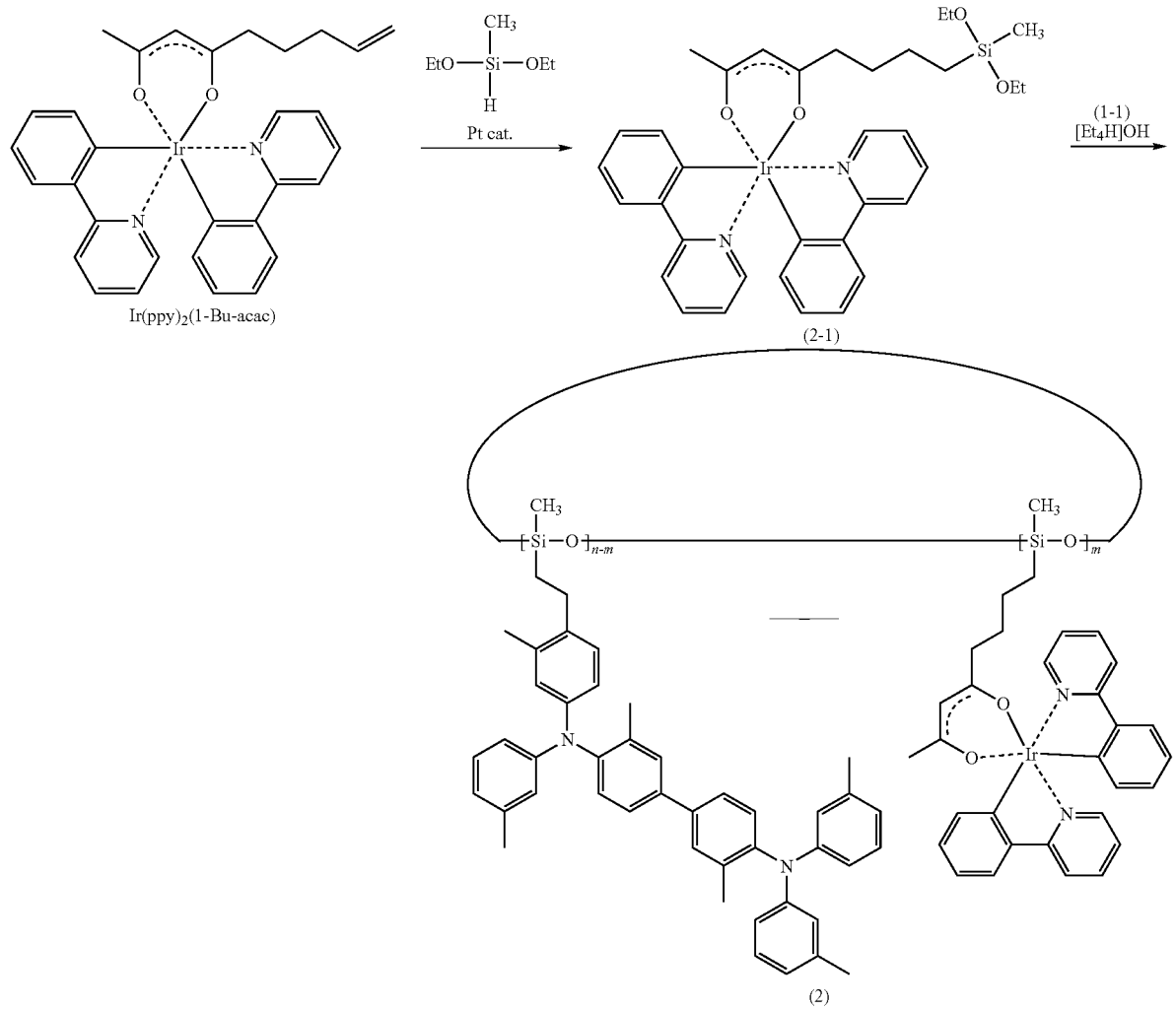

Description will be given with reference to the above-mentioned scheme.

Synthesis of Compound (2-1)

100 mg of Ir(ppy)₂(1-Bu-acac) synthesized by the method described in JP 2003-113246 A was put in a three-necked recovery flask. After the replacement of inside of the recovery flask with nitrogen, 2 mL of anhydrous toluene was added to the flask to dissolve the Ir(ppy)₂(1-Bu-acac). To this toluene solution was added 320 μL of diethoxymethylsilane and 64 mg of a xylene solution containing 3% platinum(0)-1,3-divinyl-1,1,3,3-tetramethyldisiloxane complex (Aldrich reagent). The resulting mixture was stirred at room temperature for 2 hours for reaction. After the reaction, the solvent was evaporated, and the residue was purified by silica gel column chromatography (eluent: chloroform/hexane=gradient from 1/1 to chloroform). The eluent was evaporated, and the residue was vacuum-dried to give the objective compound.

The amount of the compound was 85 mg, and the yield was 72%. Identification was performed by $^1$H-NMR.

$^1$H-NMR (270 MHz, CDCl$_3$) ppm: 8.49 (d, J=5.7 Hz, 2H, ArH), 7.83 (t, J=7.8 Hz, 2H, ArH), 7.70 (m, 2H, ArH), 7.54 (t, J=6.8 Hz, 2H, ArH), 7.10 (m, 2H, ArH), 6.80 (t, J=7.3 Hz, 2H, ArH), 6.68 (m, 2H, ArH), 6.35 (d, J=6.2 Hz, 1H, ArH), 6.25 (d, J=6.2 Hz, 1H, ArH), 5.19 (s, 1H, acac-methine), 2.01 (t, J=7.3 Hz, 2H, —CH$_2$—), 1.79 (s, 3H, CH$_3$), 1.72 (m, 2H, —CH$_2$—), 1.38 (m, 2H, —CH$_2$—), 1.25 (m, 2H, —CH$_2$—), 0.22 (t, 2H, SiCH$_2$—), 0.12 (s, 3H, SiCH$_3$).

Synthesis of Compound (2)

180 mg of the compound (1-1) and 20 mg of the compound (2-1) were put in a three-necked recovery flask. After the replacement of inside the recovery flask with nitrogen, 3 mL of anhydrous THF was added to the flask to dissolve the compound (1-1) and the compound (2-1). To this THF solution was added 100 mg of an aqueous solution containing 20% tetraethylammonium hydroxide. The resulting mixture was stirred at room temperature for 24 hours for reaction. After the reaction, one drop of acetic acid was added to the reaction solution for neutralization. The solvent was evaporated, and the residue was purified by silica gel chromatography (eluent: chloroform/hexane=gradient from 1/3 to 1/1). The eluent was evaporated, and the residue was dissolved in a small amount of acetone and was dropwise added to a large amount of methanol for precipitation. The resulting precipitate was collected by filtration and was vacuum-dried to give a compound (2) as a light yellow powder.

The amount of the compound was 172 mg. Identification was performed by MALDI-TOF-MS. The MALDI-TOF-MS confirmed that the resulting compound (2) was a mixture of a compound of n=4 and m=0, a compound of n=4 and m=1, and a compound of n=4 and m=2.

Example 3

Synthesis of Cyclic Siloxane Compound (3)

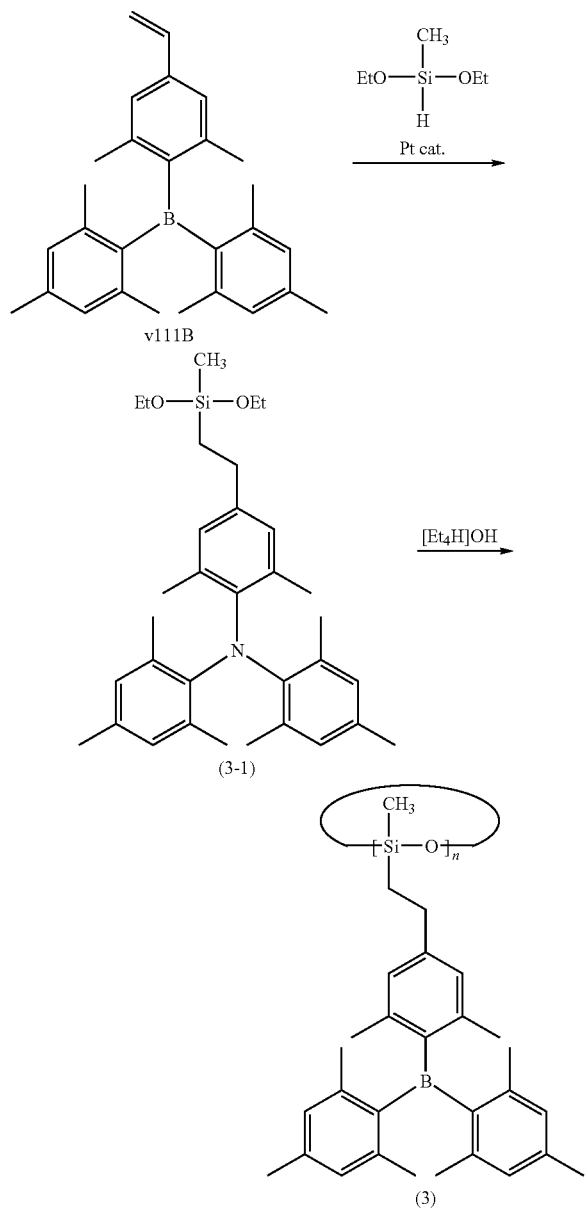

Description will be given with reference to the above-mentioned scheme.
Synthesis of Compound (3-1)
352 mg of v111B was put in a three-necked recovery flask. After the replacement of inside of the recovery flask with nitrogen, 5 mL of anhydrous toluene was added to the flask to dissolve the v111B. To this toluene solution was added 320 μL of diethoxymethylsilane and 127 mg of a xylene solution containing 3% platinum(0)-1,3-divinyl-1,1,3,3-tetramethyldisiloxane complex (Aldrich reagent). The resulting mixture was stirred at room temperature for 2 hours for reaction. After the reaction, the solvent was evaporated, and the residue was purified by silica gel column chromatography (eluent: chloroform/hexane=1/3 to 3/1). The eluent was evaporated, and the residue was vacuum-dried to give a compound (3-1).

The amount of the compound was 139 mg, and the yield was 29%. Identification was performed by $^1$H-NMR.

$^1$H-NMR (270 MHz, CDCl$_3$) ppm: 6.75 (s, 2H, ArH), 6.73 (s, 4H, ArH), 3.78 (q, 4H, —OCH$_2$—), 2.62 (m, 2H, —CH$_2$—), 2.26 (s, 6H, —CH$_3$), 1.97 (m, 18H, —CH$_3$), 1.23 (t, 6H, —OCH$_2$CH$_3$), 0.98 (m, 2H, —CH$_2$—), 0.09 (s, 3H, SiCH$_3$).

Synthesis of Compound (3)
100 mg of the compound (3-1) was put in a three-necked recovery flask. After the replacement of inside of the recovery flask with nitrogen, 1.5 mL of anhydrous THF was added to the flask to dissolve the compound (3-1). To this THF solution was added 50 mg of an aqueous solution containing 20% tetraethylammonium hydroxide. The resulting mixture was stirred at room temperature for 24 hours for reaction. After the reaction, one drop of acetic acid was added to the reaction solution for neutralization. The solvent was evaporated, and the residue was purified by silica gel chromatography (eluent: chloroform/hexane=1/3). The eluent was evaporated, and the residue was dissolved in a small amount of acetone and was dropwise added to a large amount of methanol for precipitation. The resulting precipitate was collected by filtration and was vacuum-dried to give a compound (3) as a white powder.

The amount of the compound was 85 mg, and the yield was 95%. Identification was performed by $^1$H-NMR and MALDI-TOF-MS. The MALDI-TOF-MS confirmed that the main component of the compound (3) was a cyclic tetramer (n=4).

$^1$H-NMR (270 MHz, CDCl$_3$) ppm: 7.50-7.35 (m, 4H, ArH), 7.16-6.96 (m, 6H, ArH), 6.82-6.65 (m, 11H, ArH), 2.63 (m, 2H, —CH$_2$—), 2.24-2.04 (m, 18H, —CH$_3$), 0.89 (m, 2H, —CH$_2$—), 0.16 (m, 3H, SiCH$_3$).

Comparative Example 1

Synthesis of Polysiloxane Compound (4)

30.1 mg of Polymethylhydrosiloxane (Aldrich reagent, Mn=1700 to 3200) and 359 mg of vHMTPD were put in a flask. After the replacement of inside of the recovery flask with nitrogen, 5 mL of anhydrous toluene was added to the flask to dissolve the polymethylhydrosiloxane and the vHMTPD. To this THF solution was added 64 mg of a xylene solution containing 3% platinum(0)-1,3-divinyl-1,1,3,3-tetramethyldisiloxane complex (Aldrich reagent). The resulting mixture was stirred at 50° C. for 67 hours for reaction. After the reaction, the solvent was evaporated, and the residue was dissolved in a small amount of chloroform and was dropwise added to methanol for precipitating polymers. A similar process was repeated for purification using a combination of chloroform/acetone and a combination of dichloromethane/methanol in sequence, instead of the combination of chloroform/methanol. Finally, a polymer was given as a slightly brown powder.

The amount of the polymer was 205 mg. Identification was performed by GPC.

GPC: Mn: 20000, Mw: 48100, Mw/Mn: 2.40

Comparative Example 1A

After the reaction of polymethylhydrosiloxane and vHMTPD by the same procedure of Comparative Example 1, purification by silica gel chromatography (eluent: chloroform) was tried instead of the purification by reprecipitation, but the polymer was tightly adsorbed to the silica gel and therefore could not be recovered.

Comparative Example 2

Synthesis of Polysiloxane Compound (5)

30.1 mg of Polymethylhydrosiloxane (Aldrich reagent, Mn=1700 to 3200), 323 mg of vHMTPD, and 39 mg of Ir(ppy)$_2$(1-Bu-acac) were put in a flask. After the replacement of inside of the flask with nitrogen, 5 mL of anhydrous toluene was added to the flask to dissolve these compounds. To this toluene solution was added 64 mg of a xylene solution containing 3% platinum(0)-1,3-divinyl-1,1,3,3-tetramethyldisiloxane complex (Aldrich reagent). The resulting mixture was stirred at 50° C. for 48 hours for reaction. After the reaction, the solvent was evaporated, and the residue was dissolved in a small amount of chloroform and was dropwise added to methanol for precipitating a polymer. A similar process was repeated using a combination of chloroform/acetone and a combination of dichloromethane/methanol in sequence, instead of the combination of chloroform/methanol. Finally, a polymer was given as a slightly brown, light yellow powder. The amount of the polymer was 198 mg. Identification was performed by GPC.

GPC: Mn: 18500, Mw: 49200, Mw/Mn: 2.66

Example 4

Production of Organic EL Device and Evaluation of EL Luminescent Property

An organic EL device was produced using a substrate having ITO (indium tin oxide) (Nippo Electric Co., Ltd.), which is a glass substrate of 25 mm square whose one surface is provided with two ITO electrodes having a width of 4 mm arranged in a stripe form as anodes. First, poly(3,4-ethylenedioxythiophene):poly(styrene sulfonate) (Bayer, trade name "Baytron P") was applied on the ITO (anode) of the substrate having ITO by spin coating under conditions of a rotation number of 3500 rpm and a coating time of 40 seconds, and the coating was dried under reduced pressure in a vacuum dryer at 60° C. for 2 hours to form an anode buffer layer. The resulting anode buffer layer has a thickness of about 50 nm.

Then, a coating solution for forming a luminescent layer was prepared. That is, 45 mg of compound (1) synthesized in Example 1, 45 mg of TMB (refer to the following formula):

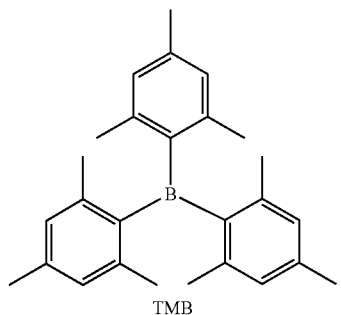

TMB and 10 mg of Ir(ppy)$_2$(acac) (refer to the following formula):

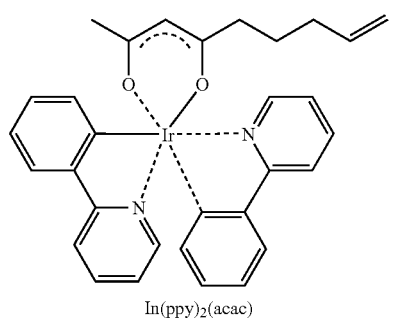

In(ppy)$_2$(acac)

were dissolved in 2900 mg of toluene (Wako Pure Chemical Industries, Ltd., special grade). The resulting solution was filtered with a filter having a pore diameter of 0.2 μm to give a coating solution. Then, the prepared coating solution was applied on the anode buffer layer by spin coating under conditions of a rotation number of 3000 rpm and a coating time of 30 seconds, and the coating was dried at room temperature (25° C.) for 30 minutes to form a luminescent layer. The resulting luminescent layer had a thickness of about 100 nm. Then, the substrate provided with the luminescent layer was placed in a deposition apparatus, and cesium was deposited at a deposition rate of 0.01 nm/s to give a thickness of 2 nm (an alkali metal dispenser manufactured by SAES Getters SpA was used as the cesium source) and then aluminum was deposited at a deposition rate of 1 nm/s to give a thickness of 250 nm as a cathode. Thus, a device 1 was produced. The layers of cesium and aluminum were formed as two stripes having a width of 3 mm so as to be orthogonal to the extending direction of the anode. Four organic luminescent devices having a length of 4 mm and a width of 3 mm were produced on one glass substrate.

Programmable direct current voltage/current source TR6143 manufactured by Advantest Corp. was used for applying voltage to the organic EL device to cause light emission, and the light-emission luminance thereof was measured with a luminance meter BM-8 manufactured by Topcon Corp. The resulting turn-on voltage, maximum luminance value, and external quantum efficiency at lighting level of 100 cd/m$^2$ are shown in Table 2 (each value is the average value of four devices formed on one substrate).

Examples 5 and 6 and Comparative Examples 3 to 5

Devices 2 to 6 (Examples 5 and 6 and Comparative Examples 3 to 5) were produced by the same process as the device 1 (Example 4) except that materials shown in Table 1 were used instead of 45 mg of compound (1), 45 mg of TMB, and 10 mg of Ir(ppy)$_2$(acac), and their EL luminescent properties were evaluated by the same method as for the device 1. Table 2 shows the results. HMTPD in Table 1 represents the following compound:

TABLE 1

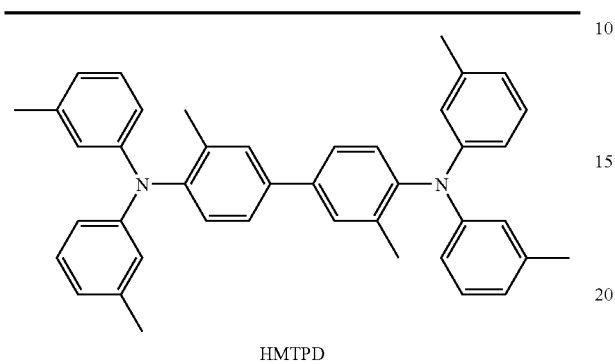

HMTPD

| Device No. | Material |
|---|---|
| 1 (Ex. 4) | compound (1): 45 mg, TMB: 45 mg, Ir(ppy)$_2$(acac): 10 mg |
| 2 (Ex. 5) | compound (2): 55 mg, TMB: 45 mg |
| 3 (Ex. 6) | compound (2): 55 mg, compound (3): 45 mg |
| 4 (Comp. Ex. 3) | HMTPD: 45 mg, TMB: 45 mg, Ir(ppy)$_2$(acac): 10 mg |
| 5 (Comp. Ex. 4) | compound (4): 45 mg, TMB: 45 mg, Ir(ppy)$_2$(acac): 10 mg |
| 6 (Comp. Ex. 5) | compound (5): 55 mg, TMB: 45 mg |

TABLE 2

| Device No. | Turn-on voltage (V) | Maximum luminance (cd/m$^2$) | External quantum efficiency (%) |
|---|---|---|---|
| 1 (Ex. 4) | 2.7 | 33000 | 5.5 |
| 2 (Ex. 5) | 2.7 | 37000 | 5.6 |
| 3 (Ex. 6) | 2.6 | 41000 | 5.9 |
| 4 (Comp. Ex. 3) | Not measured due to a short-circuit in the device | | |
| 5 (Comp. Ex. 4) | 3.1 | 12000 | 2.5 |
| 6 (Comp. Ex. 5) | 3.3 | 9800 | 3.1 |

It is confirmed from Tables 1 and 2 that in the luminescent device (device No. 4) having a luminescent layer made of only low molecular weight compounds, the luminescent layer was crystallized not to cause light emission in the device and therefore the EL luminescent properties thereof could not evaluated, but in the luminescent devices (device Nos. 1 to 3) produced using the cyclic siloxane compounds of the present invention, the EL luminescent properties thereof could be evaluated to show that favorable luminescent layers were formed. In addition, it is confirmed that in the luminescent devices (device Nos. 1 to 3) produced using the cyclic siloxane compounds of the present invention have low turn-on voltage, high maximum luminances, and high external quantum efficiencies, compared to those of the luminescent devices (device Nos. 5 and 6) having luminescent layers made of linear polysiloxane compounds used as comparative examples.

The invention claimed is:

1. A cyclic siloxane compound represented by Formula (1) below:

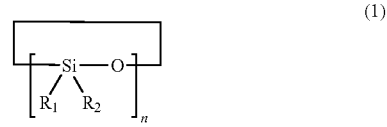

wherein, in Formula (1), R$_1$ and R$_2$ are each independently a luminescent monovalent group, a charge-transporting monovalent group, or another substituent; at least one of R$_1$ and R$_2$ is the luminescent monovalent group; and at least one of R$_1$ and R$_2$ is the charge-transporting monovalent group; and n is an integer of 2 to 100, wherein the luminescent monovalent group is obtained by substituting a hydrogen atom of a phosphorescent compound represented by any one of Formulae (E-1) to (E-49) below with a linking group X$_A$; X$_A$ is a single bond or a group represented by —(CH$_2$)$_n$—, wherein n is an integer of 1 to 20; and the luminescent monovalent group is linked to a Si atom in Formula (1) via the linking group X$_A$;

the charge-transporting monovalent group is obtained by substituting a hydrogen atom of a charge-transporting compound represented by any one of Formulae (E-50) to (E-67) below with a linking group X$_B$, and is linked to a Si atom in Formula (1) via the linking group X$_B$; X$_B$ is a single bond or a group represented by —(CH$_2$)$_n$—, wherein n is an integer of 1 to 20; and the another substituent group is selected from the group consisting of aryl groups having 6 to 60 carbon atoms, monovalent heterocyclic groups, alkyl groups having 1 to 20 carbon atoms, arylalkyl groups having 7 to 60 carbon atoms and aryloxyalkyl groups having 7 to 60 carbon atoms:

E-1

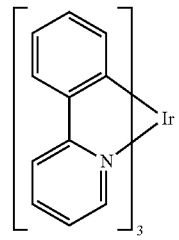

E-2

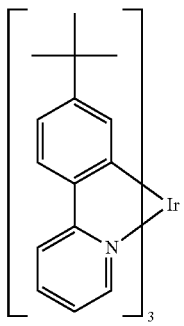

E-3
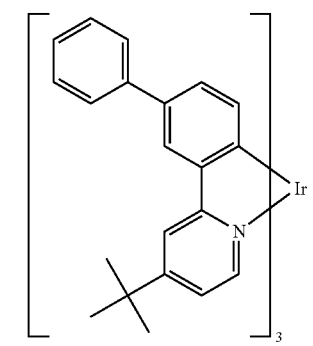
E-4
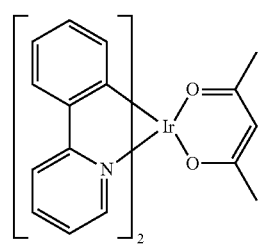
E-5
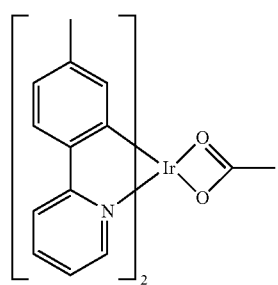
E-6
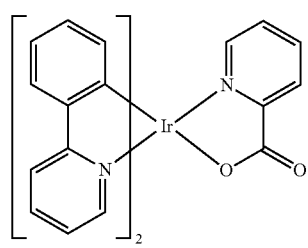
E-7
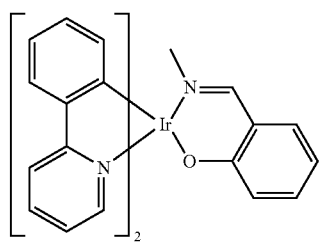
E-8
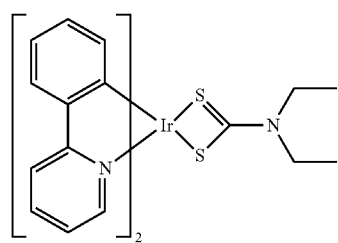
E-9
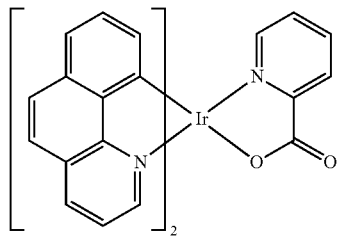
E-10
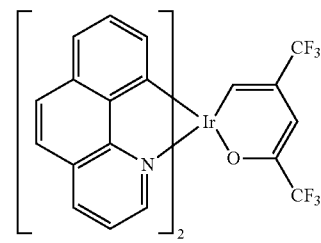
E-11
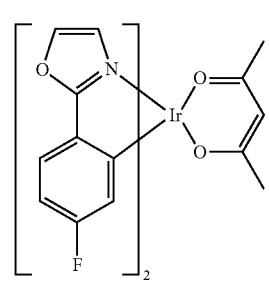
E-12
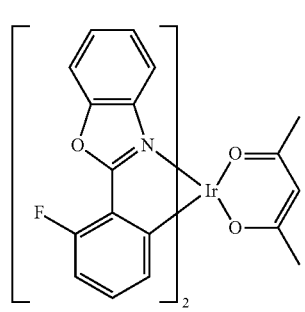
E-13
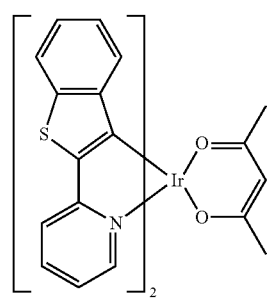

-continued
E-14
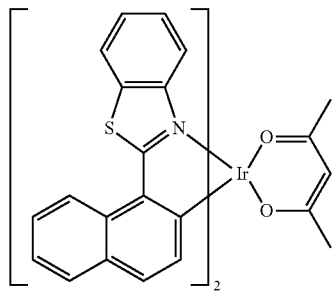
E-15
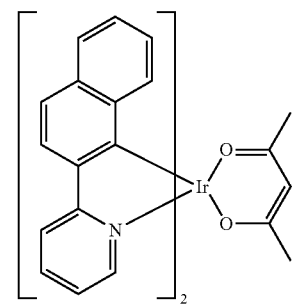
E-16
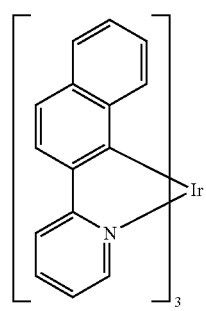
E-17
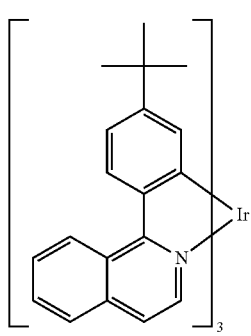
-continued
E-18
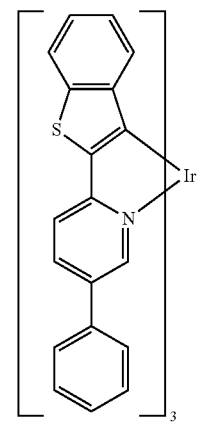
E-19
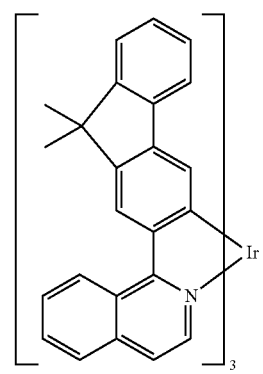
E-20
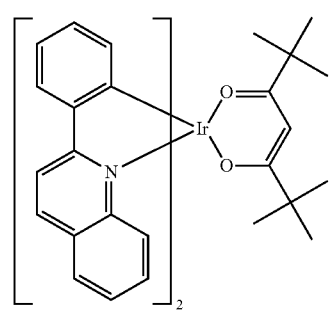
E-21
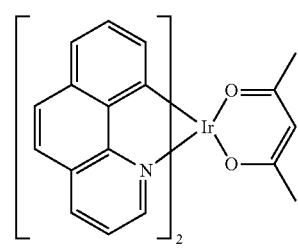
E-22
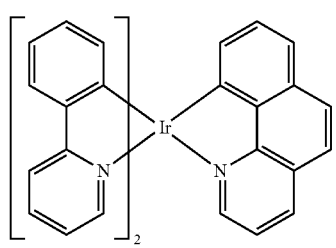

E-23
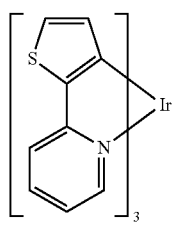
E-24
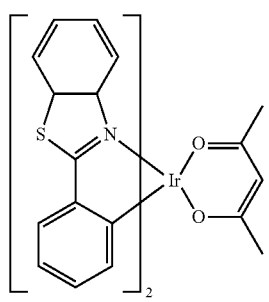
E-25
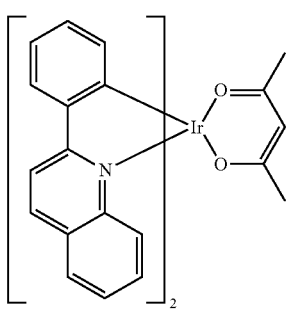
E-26
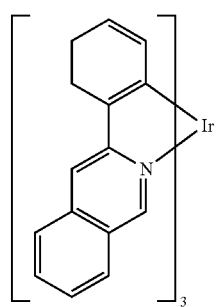
E-27
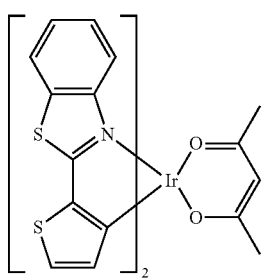
E-28
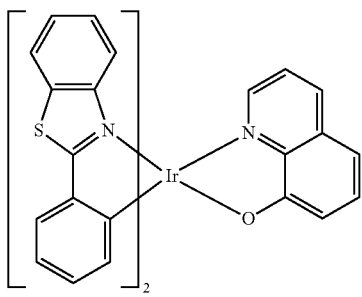
E-29
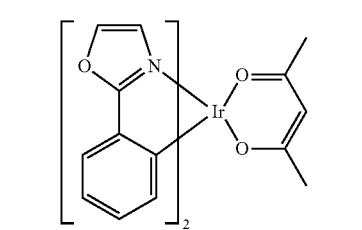
E-30
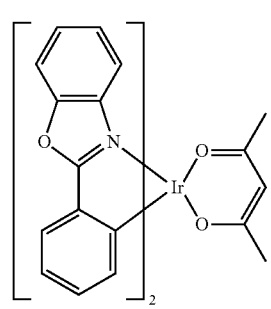
E-31
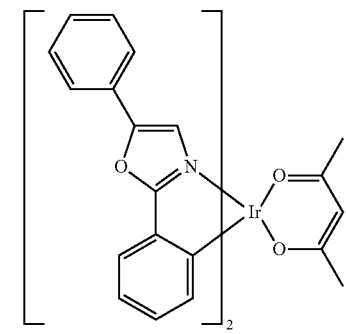
E-32
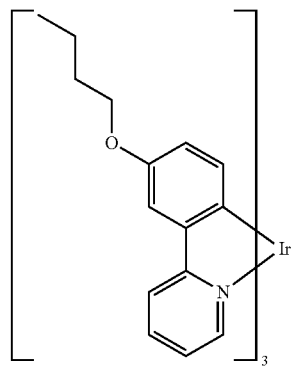

E-33 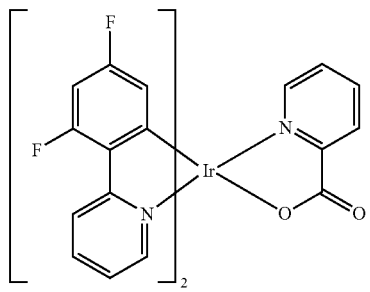
E-34 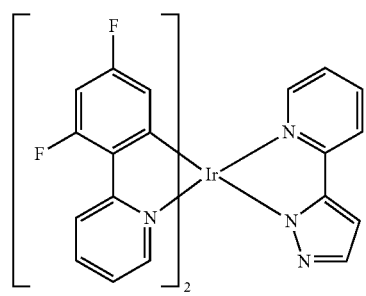
E-35 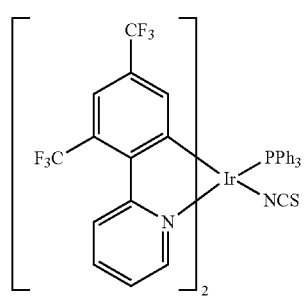
E-36 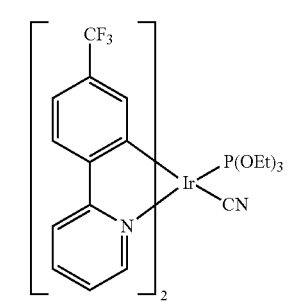
E-37 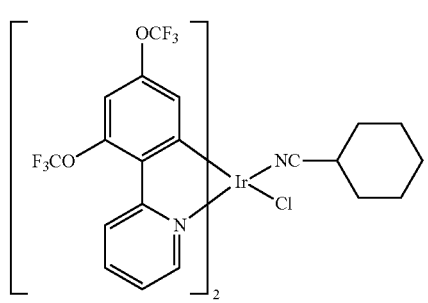
E-38 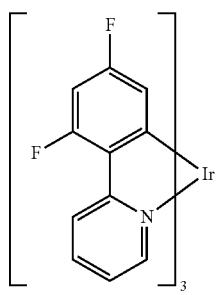
E-39 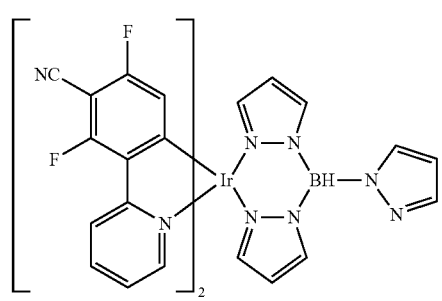
E-40 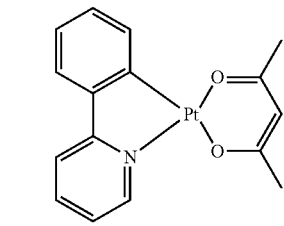
E-41 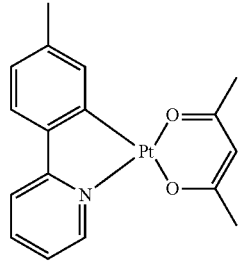
E-42 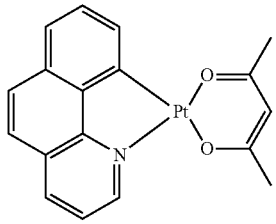
E-43 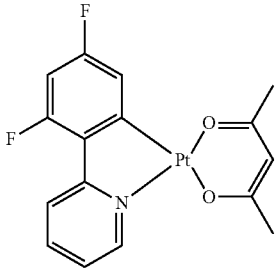

-continued
E-44
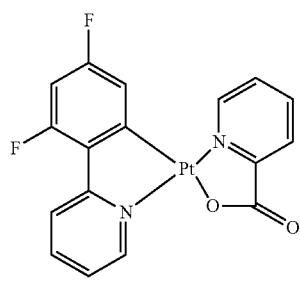
E-45
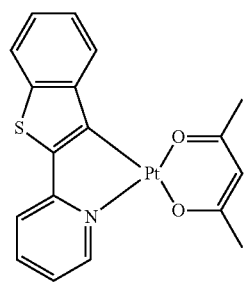
E-46
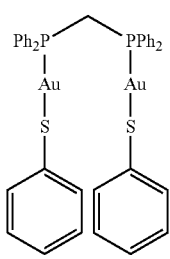
E-47
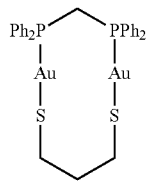
E-48
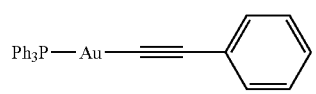
E-49
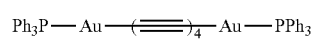
E-50
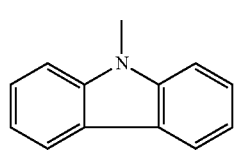
E-51
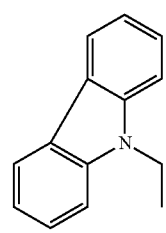
-continued
E-52
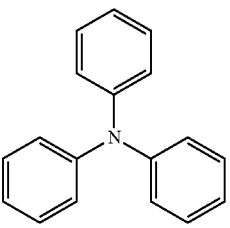
E-53
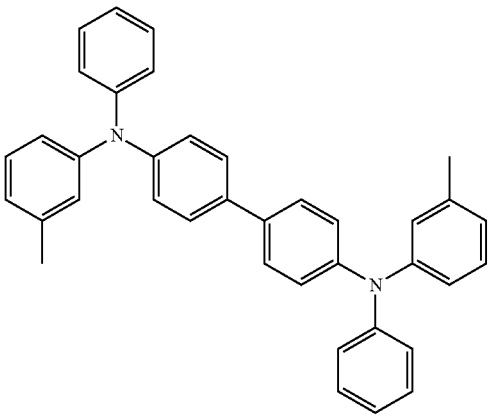
E-54
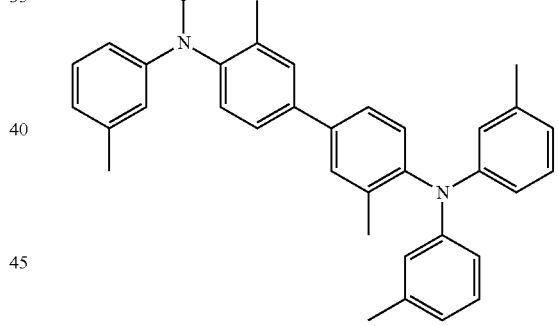
E-55
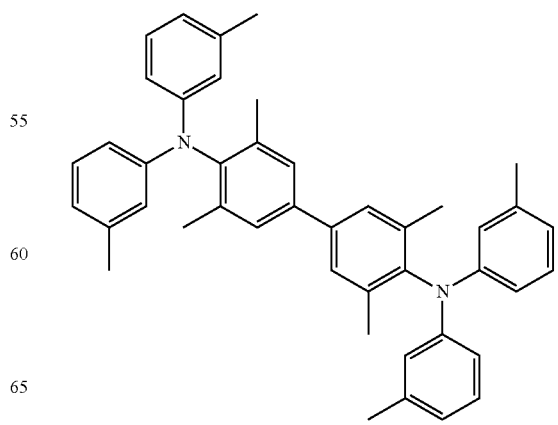

E-56
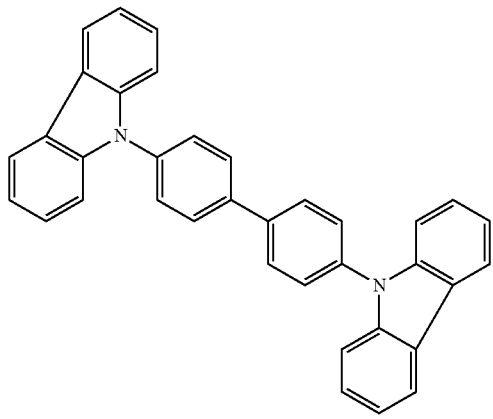
E-57
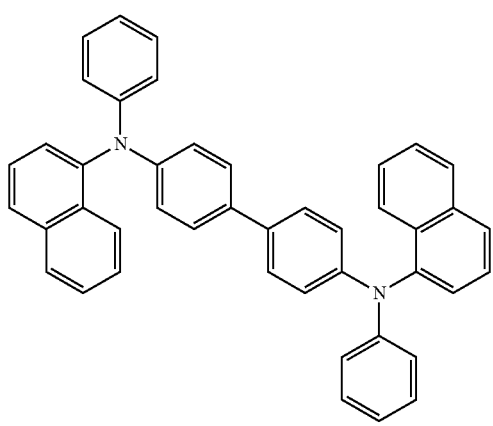
E-58
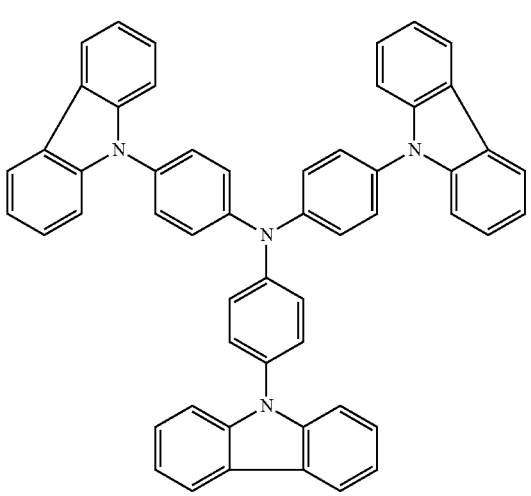
E-59
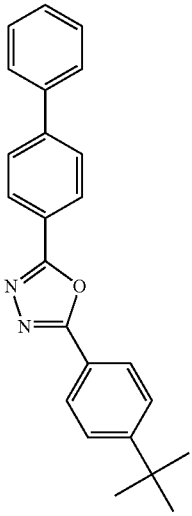
E-60
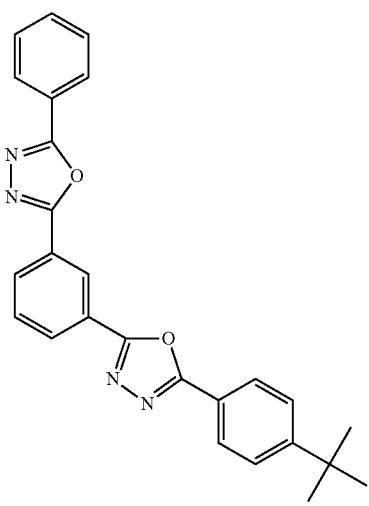
E-61
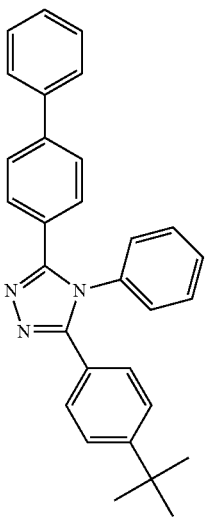

E-62
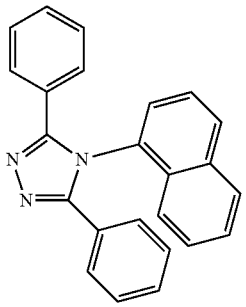

E-63
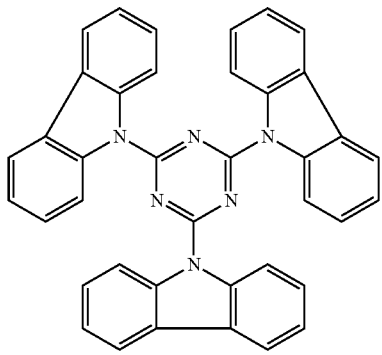

E-64
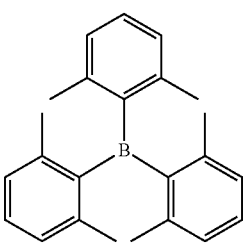

E-65
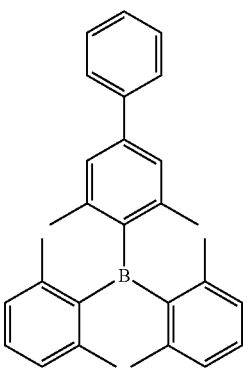

E-66
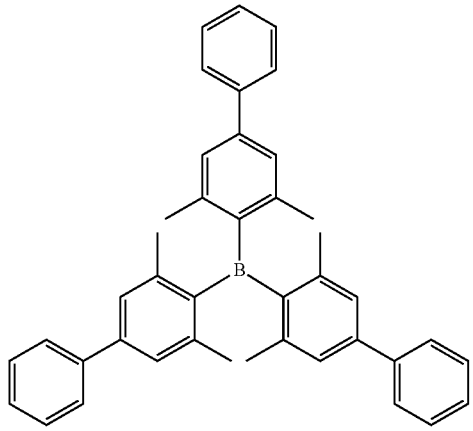

E-67
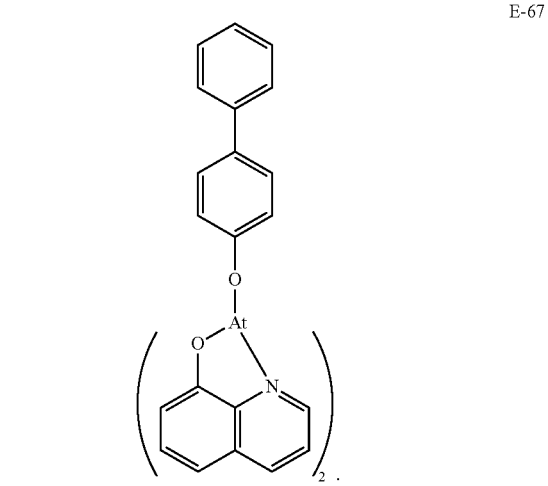

2. The cyclic siloxane compound according to claim 1, wherein the group represented by —$(CH_2)_n$—, wherein n is an integer of 1 to 20, is a group represented by —$CH_2$—$CH_2$—.

3. The cyclic siloxane compound according to claim 1, wherein at least one of $R_1$ and $R_2$ in Formula (1) is a group obtained by substituting a hydrogen atom of a triarylamine derivative with a linking group X, and is linked to a Si atom in Formula (1) via the linking group X.

4. The cyclic siloxane compound according to claim 1, wherein at least one of $R_1$ and $R_2$ in Formula (1) is a group obtained by substituting a hydrogen atom of a triarylborane derivative with a linking group X, and is linked to a Si atom in Formula (1) via the linking group X.

5. The cyclic siloxane compound according to claim 1, wherein the phosphorescent compound is an iridium complex.

6. A process of producing a cyclic siloxane compound represented by Formula (1) below:

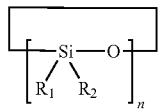
(1)

wherein, in Formula (1), $R_1$ and $R_2$ are each independently a luminescent monovalent group, a charge-transporting monovalent group, or another substituent; at least one of R₁ and R₂ is the charge-transporting monovalent group and at least one of R₁ and R₂ is the luminescent monovalent group; and n is an integer of 2 to 100, the said process comprising:

cyclocondensing monomers represented by Formula (10) below:

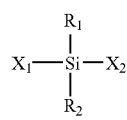
(10)

wherein, in Formula (10), $R_1$ and $R_2$ are each independently the same as $R_1$ and $R_2$ in Formula (1); and $X_1$ and $X_2$ are each independently a hydroxyl group, an alkoxy group, or a halogen atom; wherein the luminescent monovalent group is obtained by substituting a hydrogen atom of a phosphorescent compound represented by any one of Formulae (E-1) to (E-49) below with a linking group $X_A$; $X_A$ is a single bond or a group represented by —(CH₂)ₙ—, wherein n is an integer of 1 to 20; and the luminescent monovalent group is linked to a Si atom in Formula (1) via the linking group $X_A$;

the charge-transporting monovalent group is obtained by substituting a hydrogen atom of a charge-transporting compound represented by any one of Formulae (E-50) to (E-67) below with a linking group $X_B$; and is linked to a Si atom in Formula (1) via the linking group $X_B$; $X_B$ is a single bond or a group represented by —(CH₂)ₙ—, wherein n is an integer of 1 to 20; and the another substituent group is selected from the group consisting of aryl groups having 6 to 60 carbon atoms, monovalent heterocyclic groups, alkyl groups having 1 to 20 carbon atoms, arylalkyl groups having 7 to 60 carbon atoms and aryloxyalkyl groups having 7 to 60 carbon atoms:

E-1
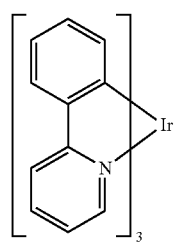

E-2
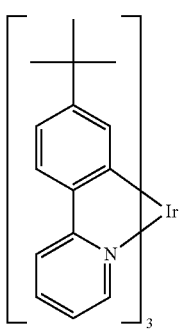

-continued

E-3
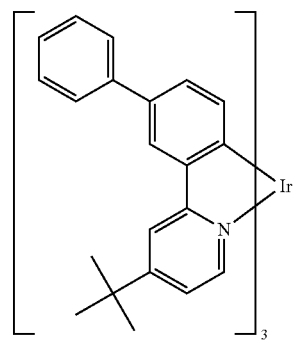

E-4
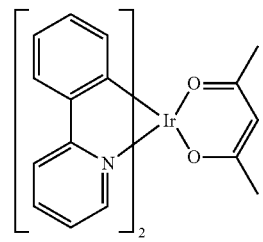

E-5
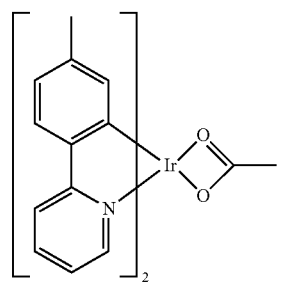

E-6
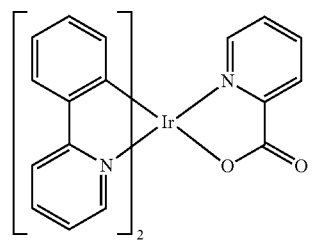

E-7
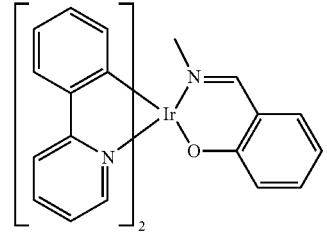

E-8
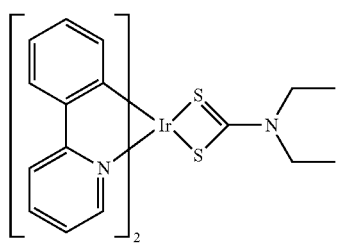

E-9
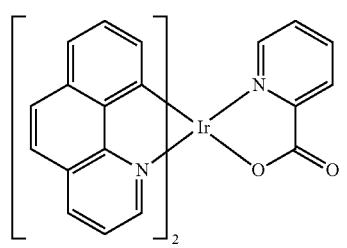
E-10
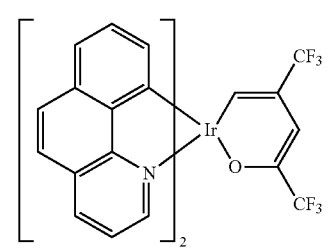
E-11
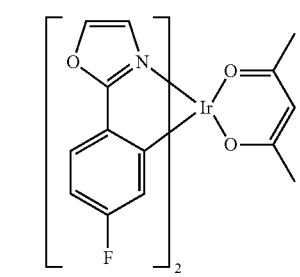
E-12
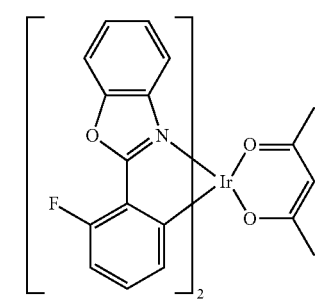
E-13
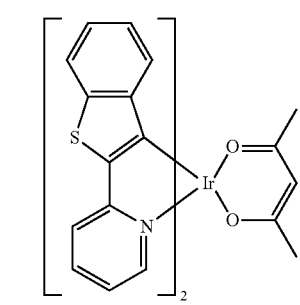
E-14
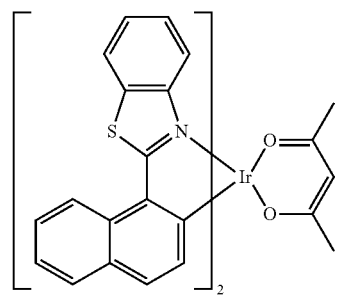
E-15
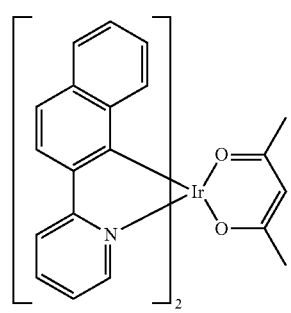
E-16
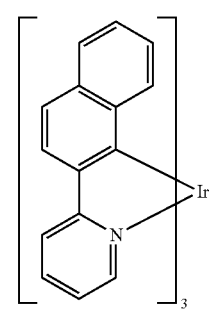
E-17
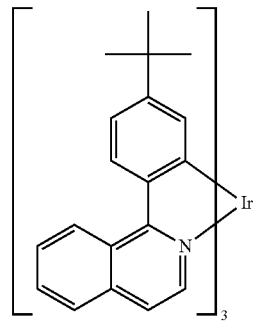

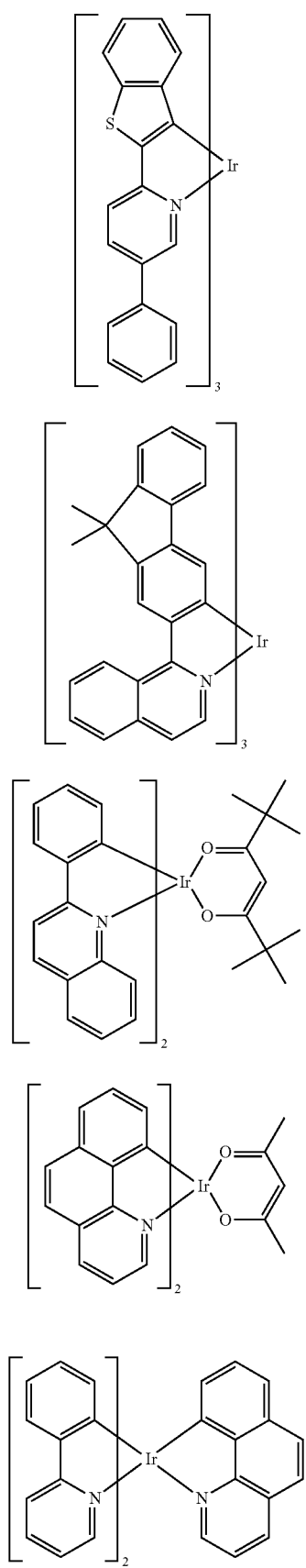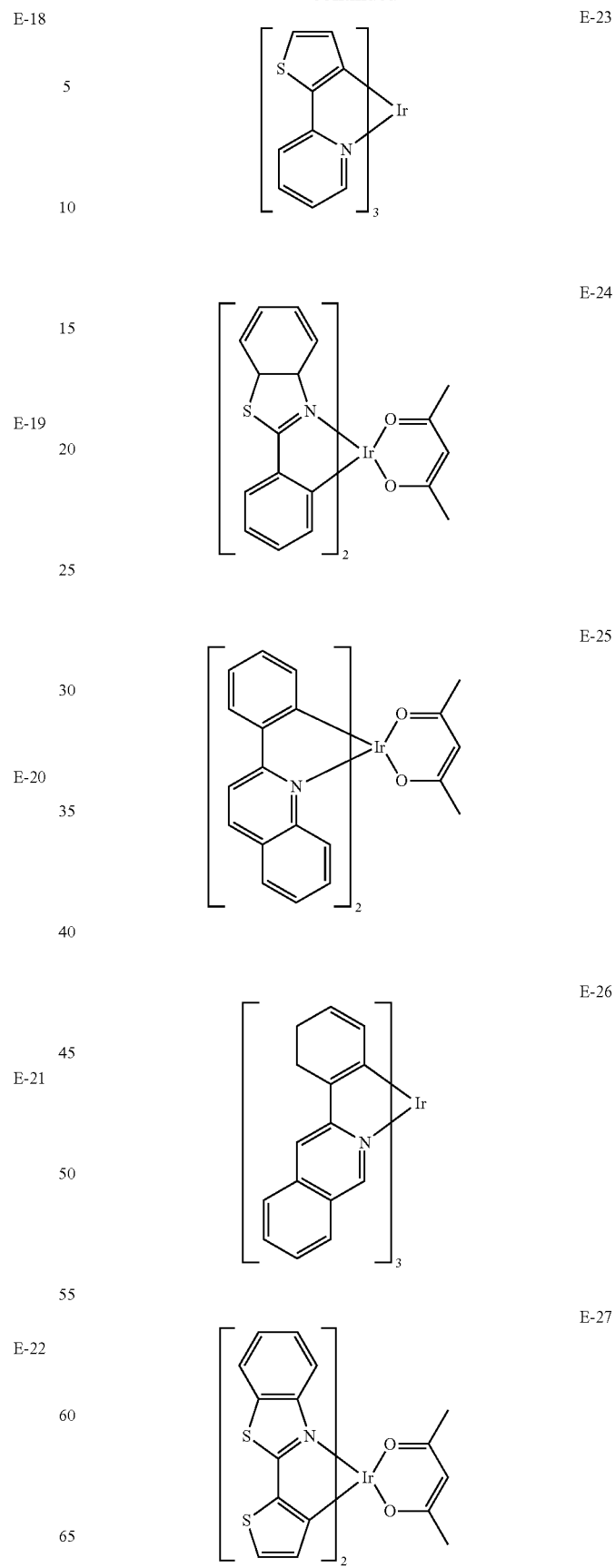

-continued
E-28
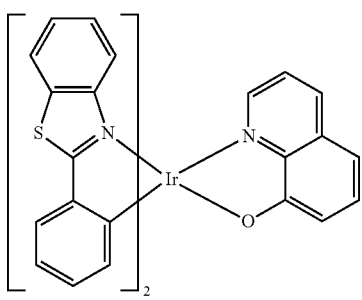
E-29
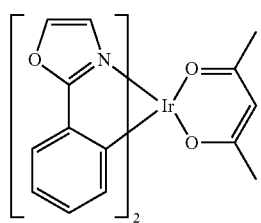
E-30
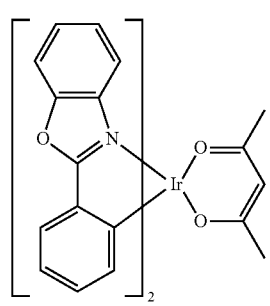
E-31
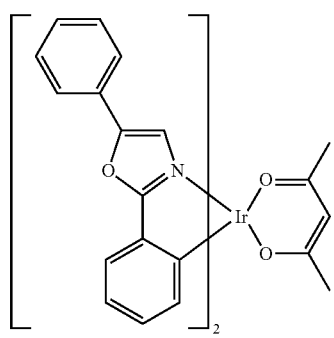
E-32
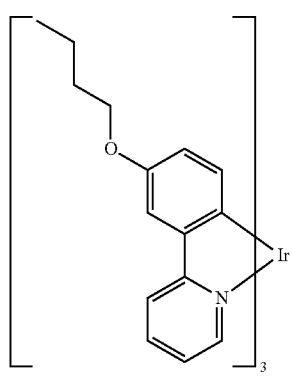
-continued
E-33
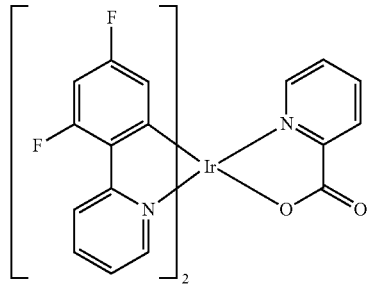
E-34
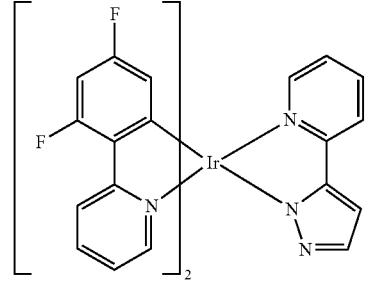
E-35
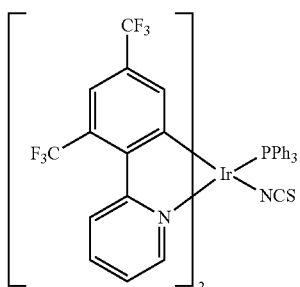
E-36
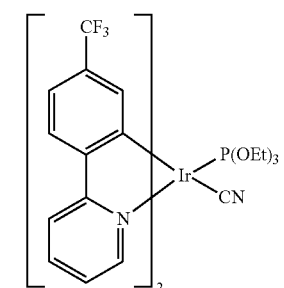
E-37
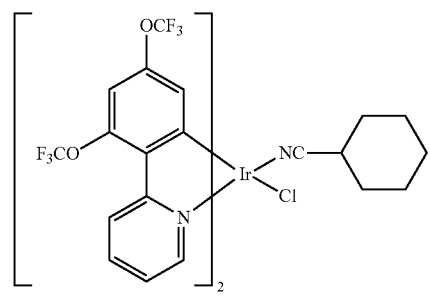

-continued

E-38

E-39

E-40

E-41

E-42

E-43

E-44

E-45

E-46

E-47

E-48

E-49

E-50

E-51

-continued
E-52
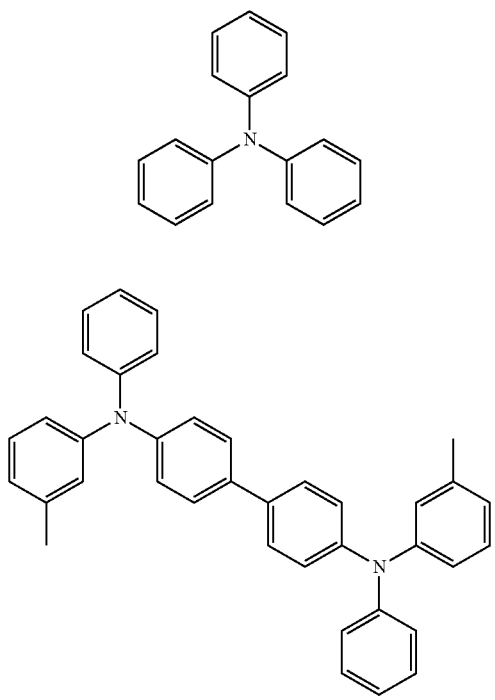
E-53
E-54
E-55
-continued
E-56
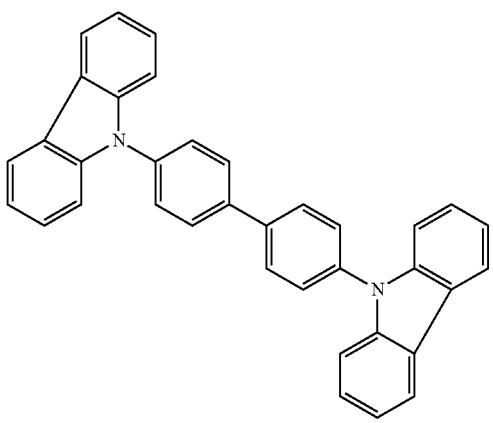
E-57
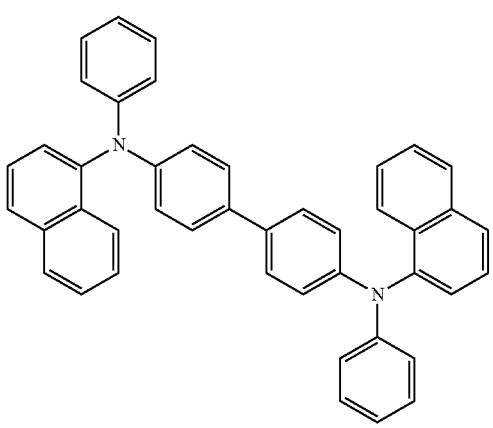
E-58
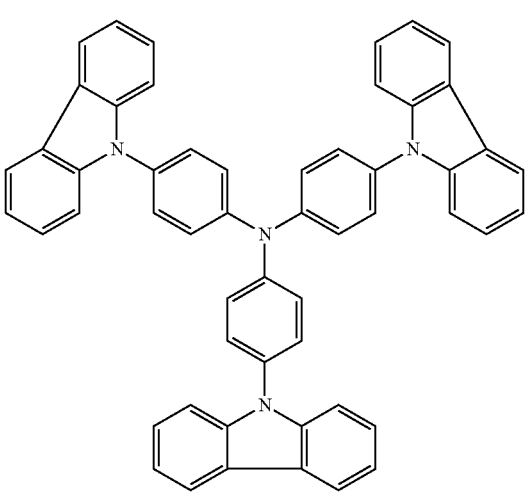
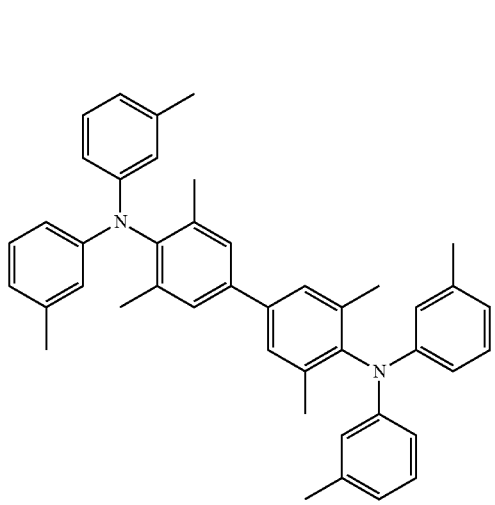

E-59
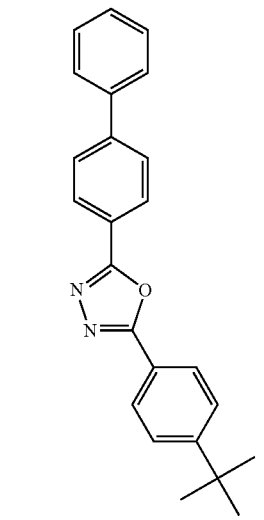
E-60
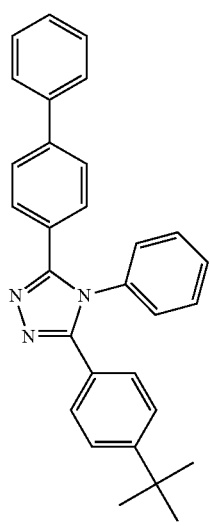
E-61
E-62
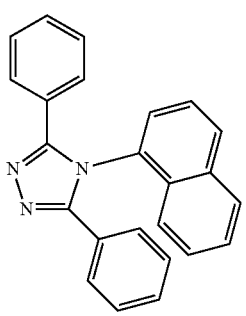
E-63
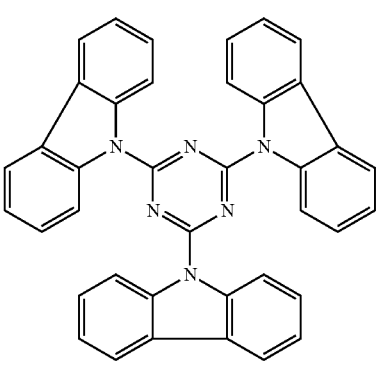
E-64
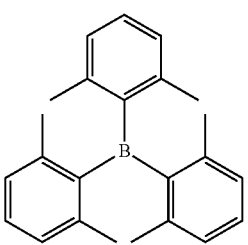
E-65
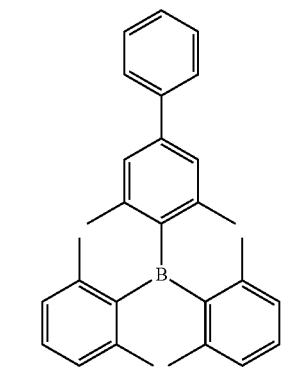

-continued

E-66

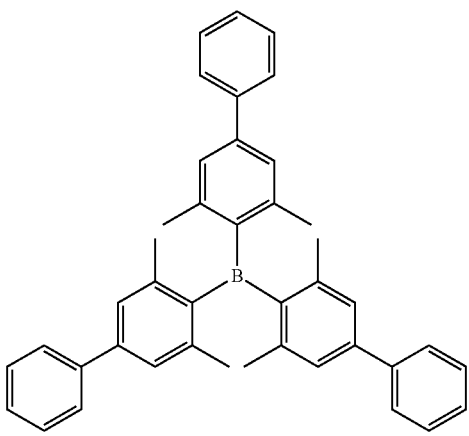

E-67

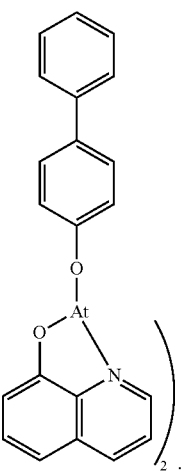

7. A process of producing a cyclic siloxane compound represented by Formula (1) below:

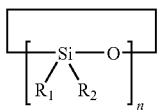
(1)

wherein, in Formula (1), R₁ and R₂ are each independently a luminescent monovalent group, a charge-transporting monovalent group, or another substituent; at least one of R₁ and R₂ is the charge-transporting monovalent group and at least one of R₁ and R₂ is the luminescent monovalent group; and n is an integer of 2 to 100, the said process comprising:

reacting a cyclic siloxane compound represented by Formula (20) below:

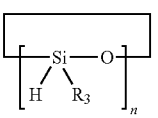
(20)

wherein, in Formula (20), R₃ is a hydrogen atom or the another substituent, and n is an integer of 2 to 100, with a charge-transporting compound having a vinyl group and capable of inducing the charge-transporting monovalent group and/or a luminescent compound having a vinyl group and capable of inducing the luminescent monovalent group; wherein the luminescent monovalent group is obtained by substituting a hydrogen atom of a phosphorescent compound represented by any one of Formulae (E-1) to (E-49) below with a linking group $X_A$; $X_A$ is a single bond or a group represented by —(CH₂)$_n$—, wherein n is an integer of 1 to 20; and the luminescent monovalent group is linked to a Si atom in Formula (1) via the linking group $X_A$;

the charge-transporting monovalent group is obtained by substituting a hydrogen atom of a charge-transporting compound represented by any one of Formulae (E-50) to (E-67 below with a linking group $X_B$, and is linked to a Si atom in Formula (1) via the linking group $X_B$; $X_B$ is a single bond or a group represented by —(CH₂)$_n$—, wherein n is an integer of 1 to 20; and the another substituent group is selected from the group consisting of aryl groups having 6 to 60 carbon atoms, monovalent heterocyclic groups, alkyl groups having 1 to 20 carbon atoms, arylalkyl groups having 7 to 60 carbon atoms and aryloxyalkyl groups having 7 to 60 carbon atoms:

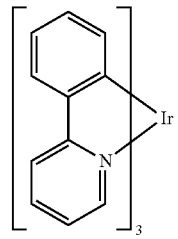
E-1

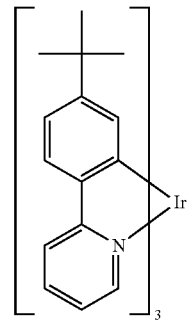
E-2

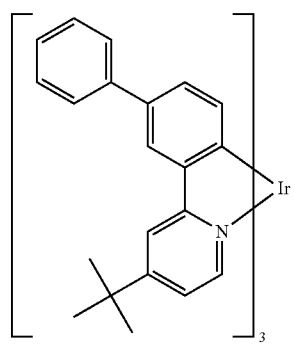
E-3

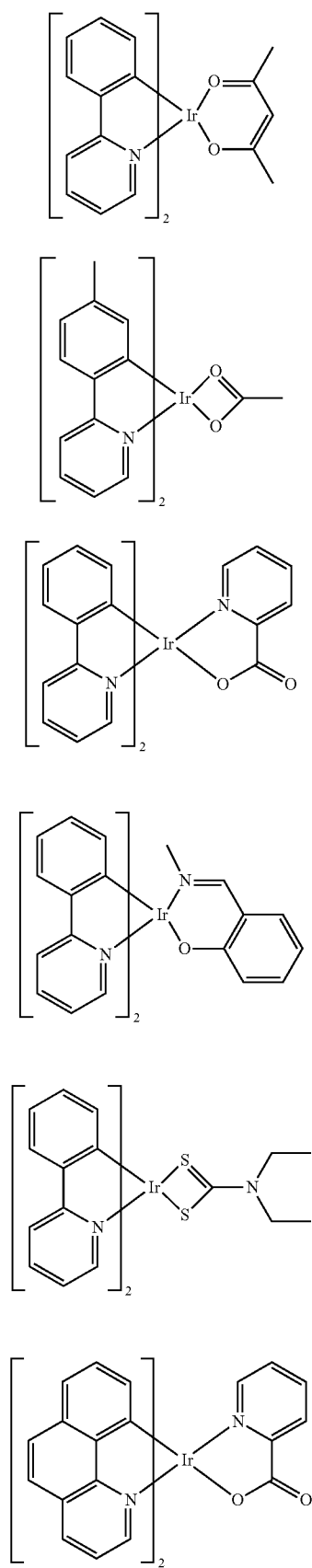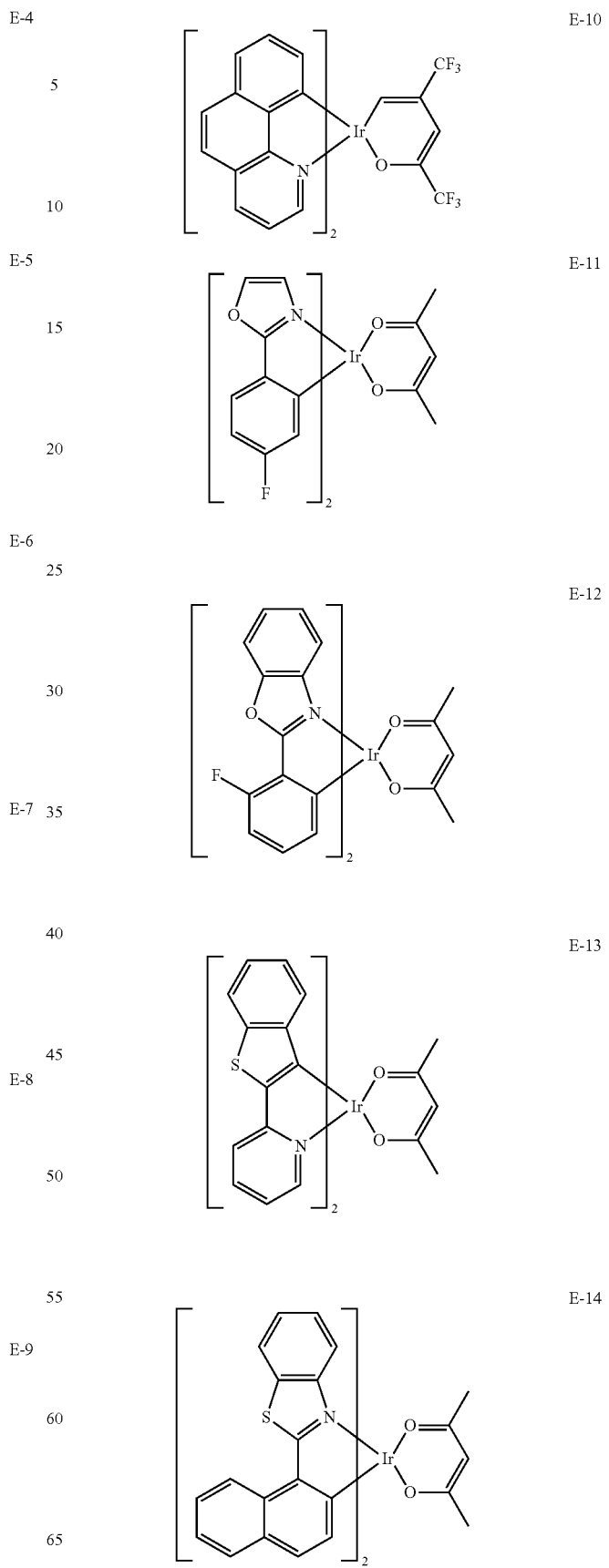

-continued
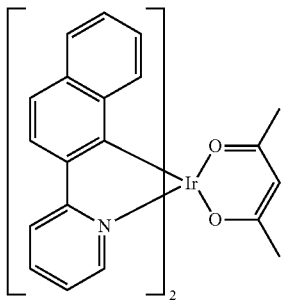
E-15
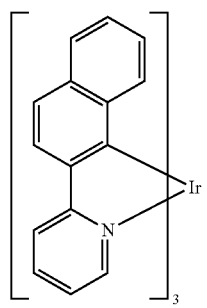
E-16
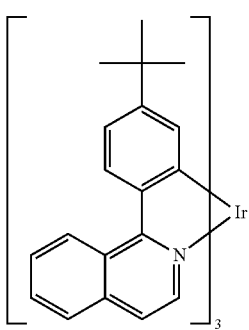
E-17
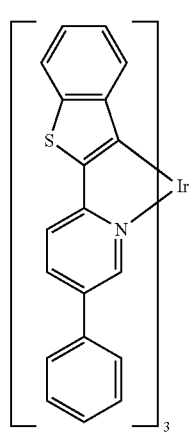
E-18
-continued
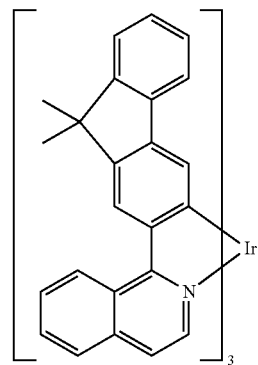
E-19
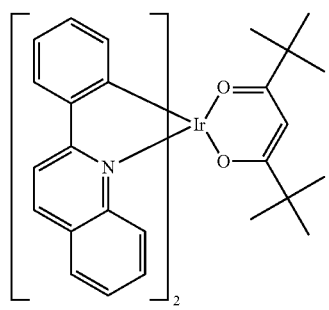
E-20
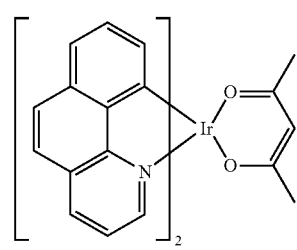
E-21
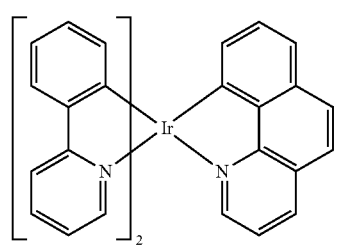
E-22
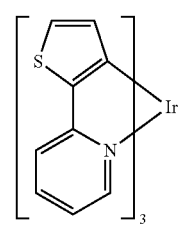
E-23

-continued
E-24
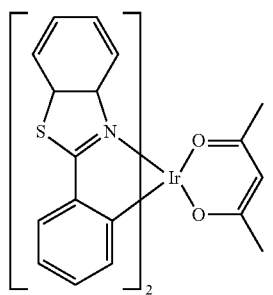
E-25
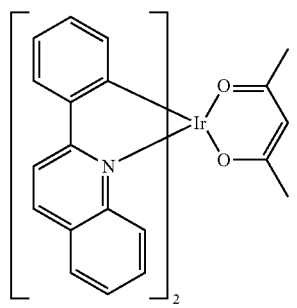
E-26
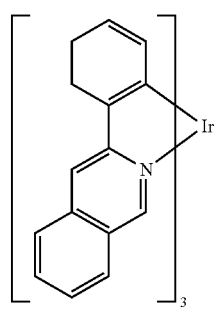
E-27
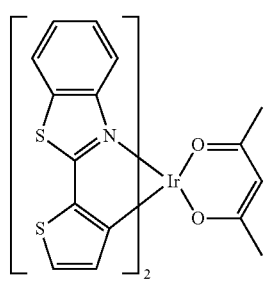
E-28
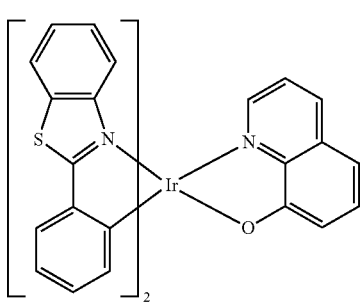
-continued
E-29
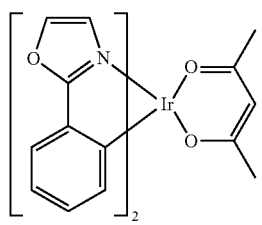
E-30
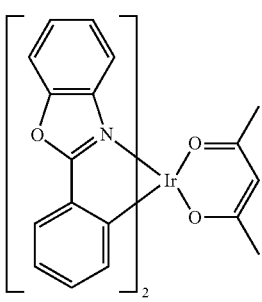
E-31
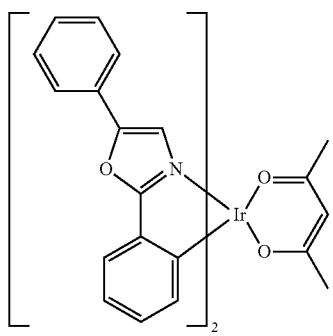
E-32
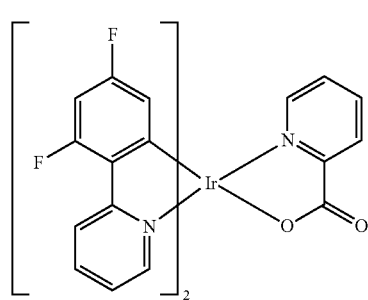
E-33

E-34 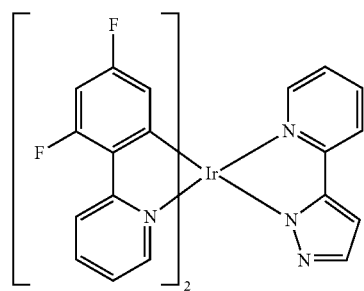
E-35 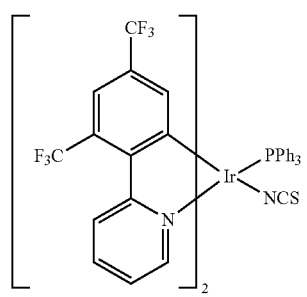
E-36 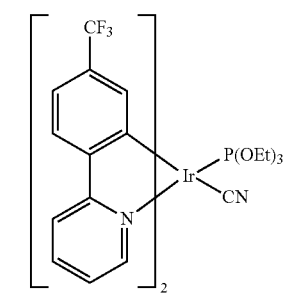
E-37 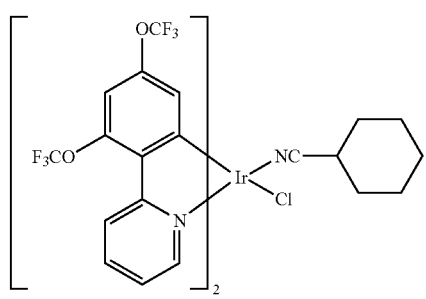
E-38 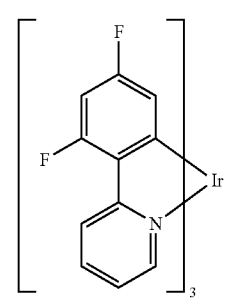
E-39 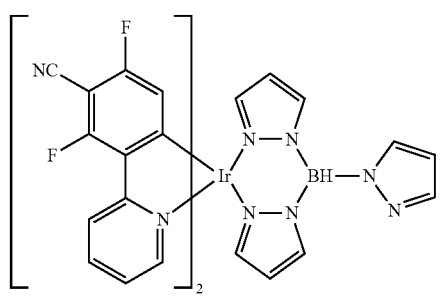
E-40 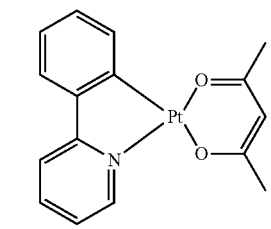
E-41 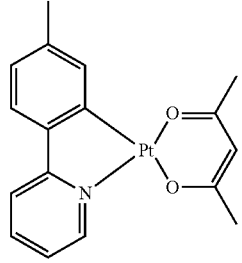
E-42 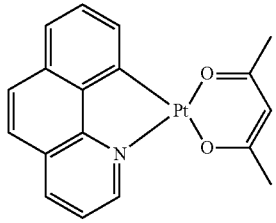
E-43 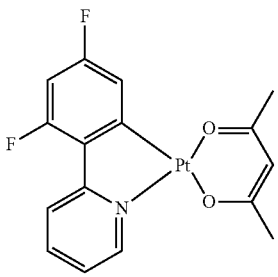
E-44 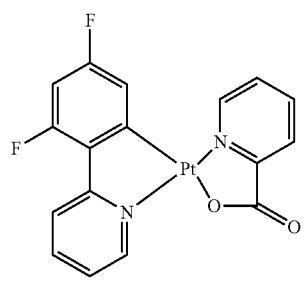

-continued
E-45
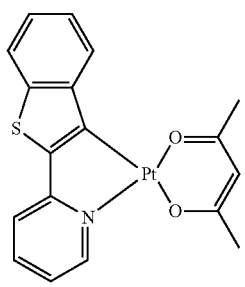
E-46
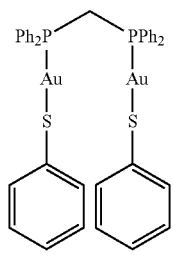
E-47
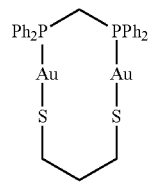
E-48
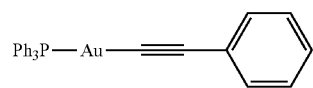
E-49
E-50
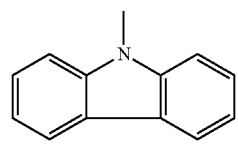
E-51
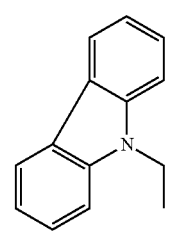
E-52
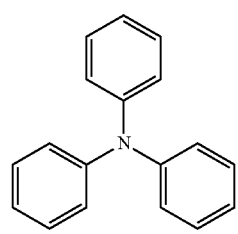
-continued
E-53
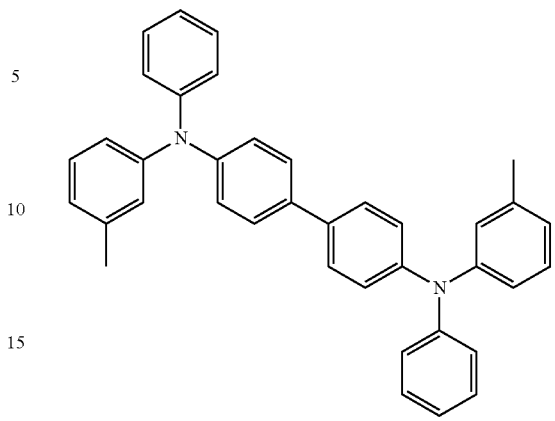
E-54
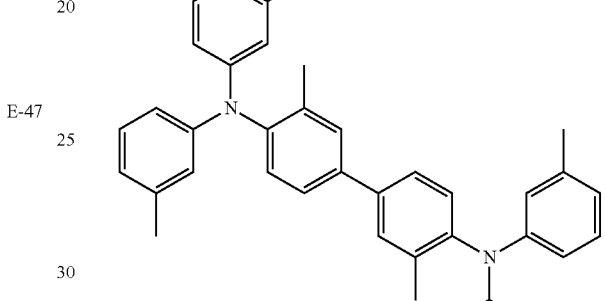
E-55
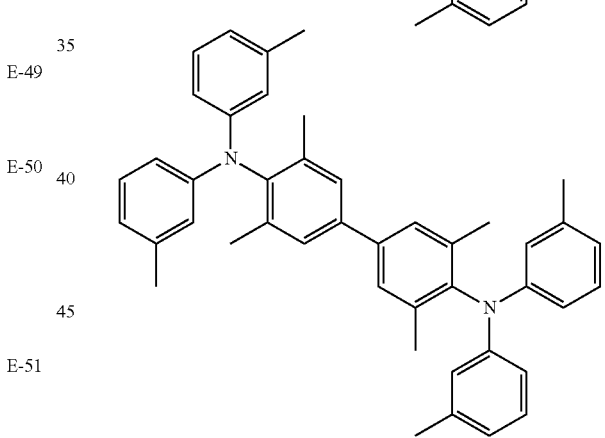
E-56
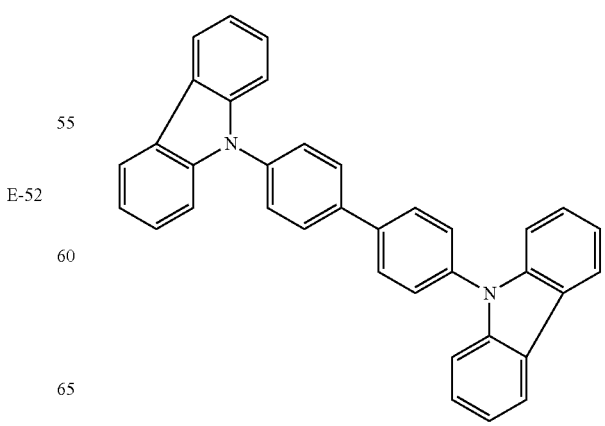

E-57
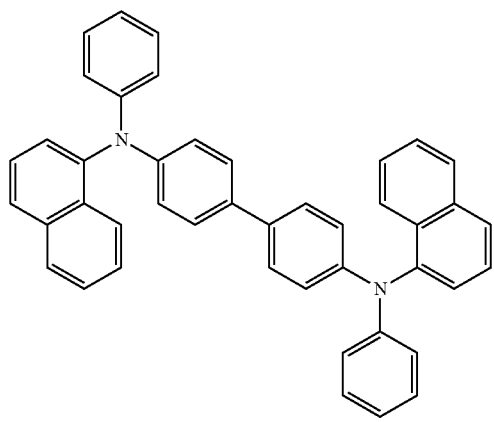
E-58
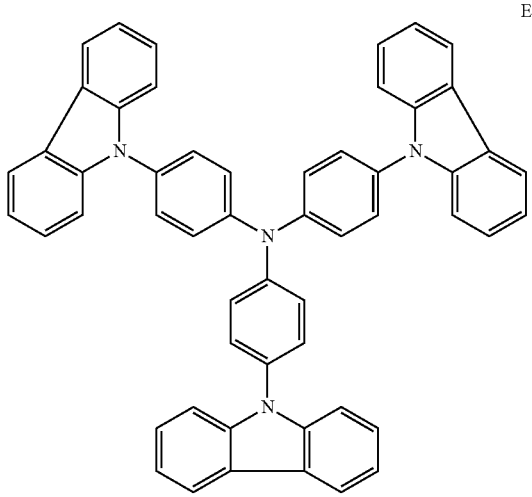
E-59
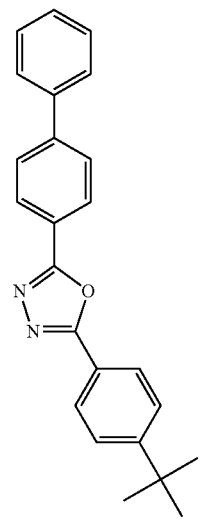
E-60
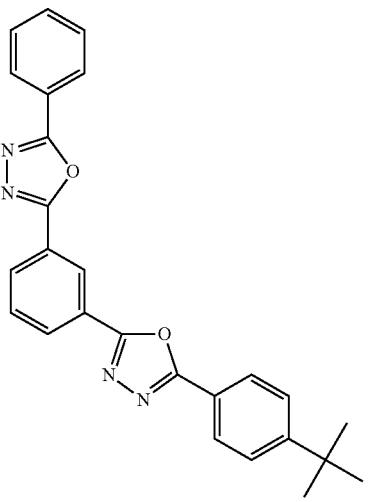
E-61
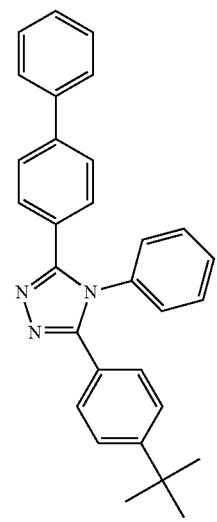
E-62
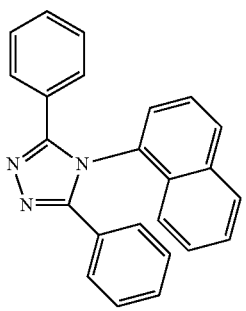

E-63

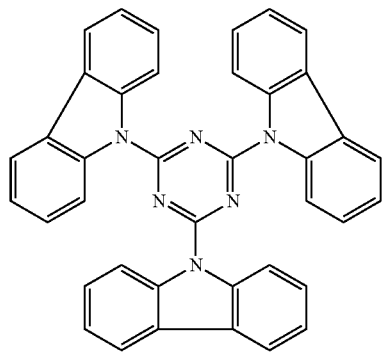

E-64

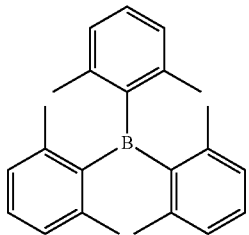

E-65

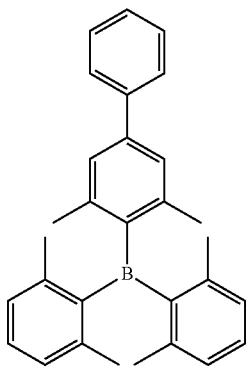

E-66

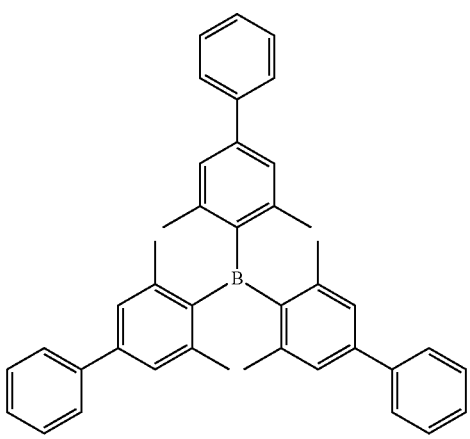

E-67

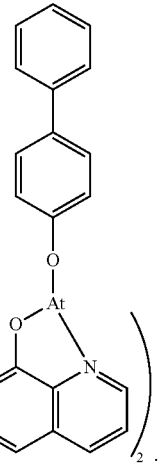

8. A process of producing a cyclic siloxane compound represented by Formula (1) below:

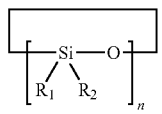
(1)

wherein, in Formula (1), $R_1$ and $R_2$ are each independently a luminescent monovalent group, a charge-transporting monovalent group, or another substituent; at least one of $R_1$ and $R_2$ is the charge-transporting monovalent group and at least one of $R_1$ and $R_2$ is the luminescent monovalent group; and n is an integer of 2 to 100, the said process comprising:

reacting a cyclic siloxane compound represented by Formula (30) below:

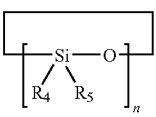
(30)

wherein, in Formula (30), $R_4$ and $R_5$ are each independently a substituent having a reactive group or the another substituent; at least one of $R_4$ and $R_5$ is the substituent having a reactive group; and n is an integer of 2 to 100, with a charge-transporting compound capable of inducing the charge-transporting monovalent group and/or a luminescent compound capable of inducing the luminescent monovalent group; wherein the luminescent monovalent group is obtained by substituting a hydrogen atom of a phosphorescent compound represented by any one of Formulae (E-1) to (E-49) below with a linking group $X_A$; $X_A$ is a single bond or a group represented by $-(CH_2)_n-$, wherein n is an integer of 1 to 20; and the luminescent monovalent group is linked to a Si atom in Formula (1) via the linking group $X_A$;

the charge-transporting monovalent group is obtained by substituting a hydrogen atom of a charge-transporting compound represented by any one of Formulae (E-50) to (E-67) below with a linking group $X_B$, and is linked to a Si atom in Formula (1) via the linking group $X_B$; $X_B$ is a single bond or a group represented by —(CH$_2$)$_n$—, wherein n is an integer of 1 to 20; and the another substituent group is selected from the group consisting of aryl groups having 6 to 60 carbon atoms, monovalent heterocyclic groups, alkyl groups having 1 to 20 carbon atoms, arylalkyl groups having 7 to 60 carbon atoms and aryloxyalkyl groups having 7 to 60 carbon atoms:

E-1
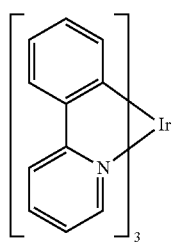

E-2
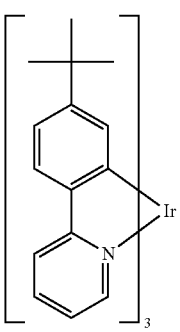

E-3
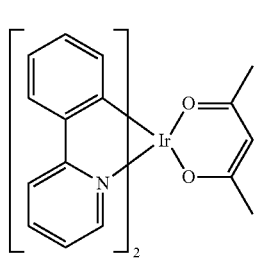

E-4
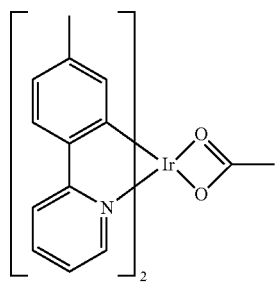

E-5
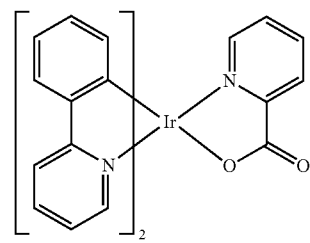

E-6
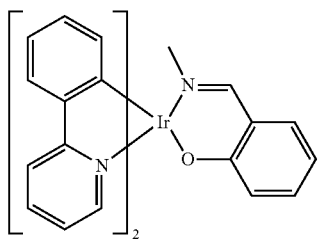

E-7
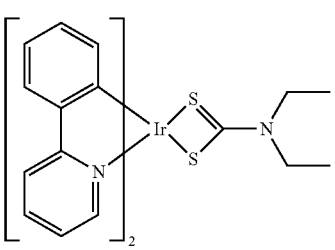

E-8
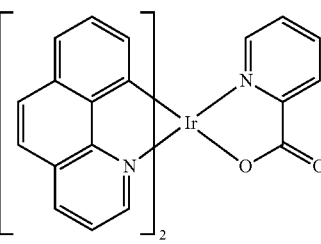

E-9
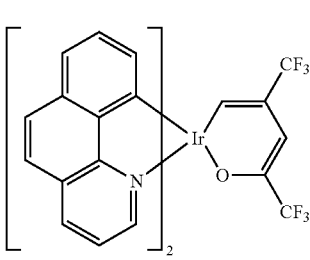

E-10

E-11 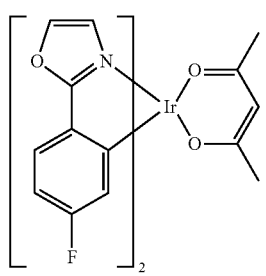
E-12 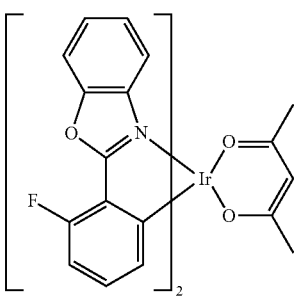
E-13 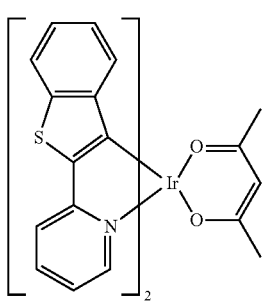
E-14 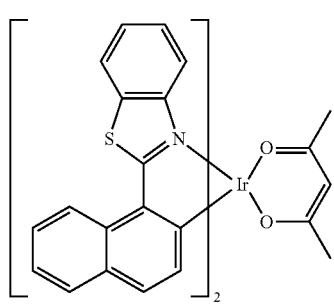
E-15 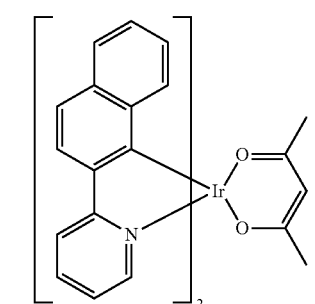
E-16 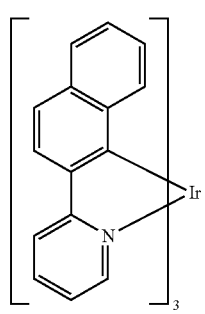
E-17 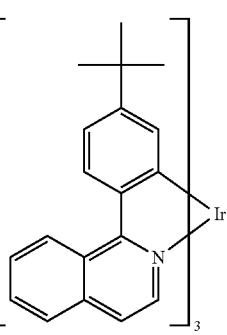
E-18 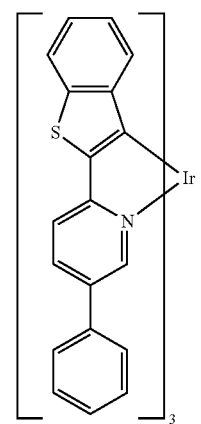
E-19 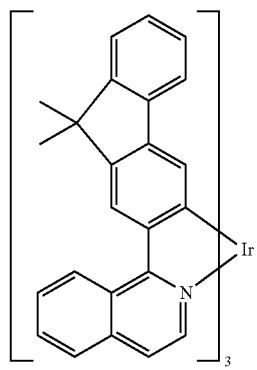

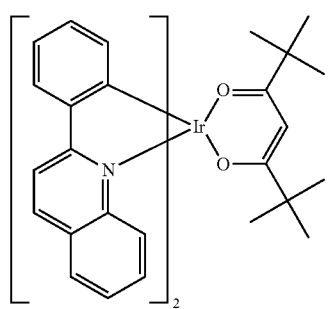 E-20
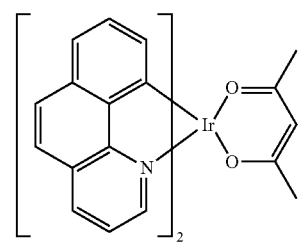 E-21
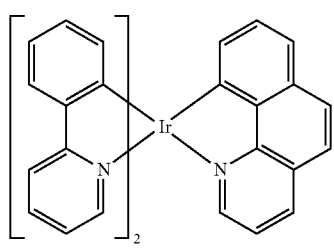 E-22
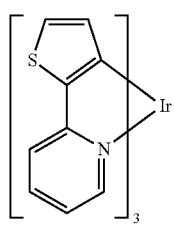 E-23
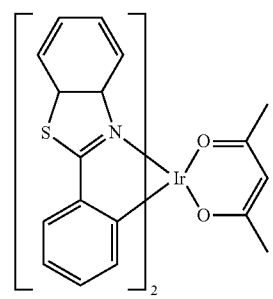 E-24
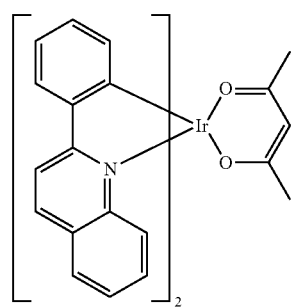 E-25
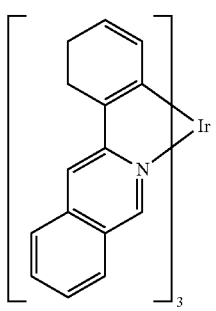 E-26
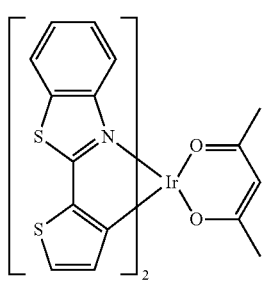 E-27
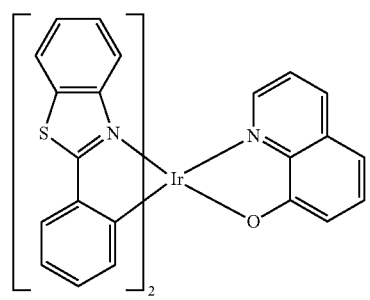 E-28
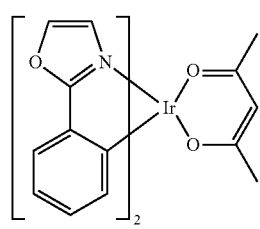 E-29
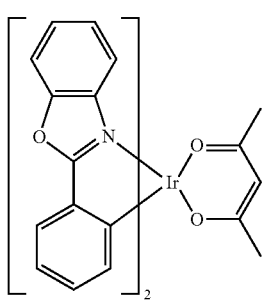 E-30

-continued
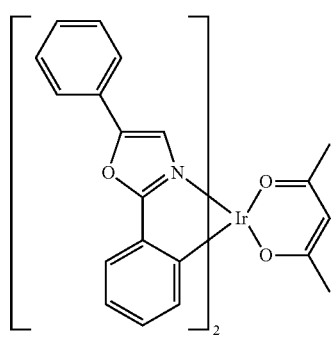 E-31
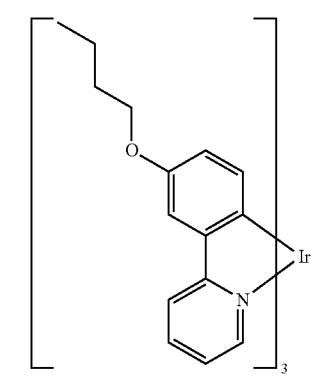 E-32
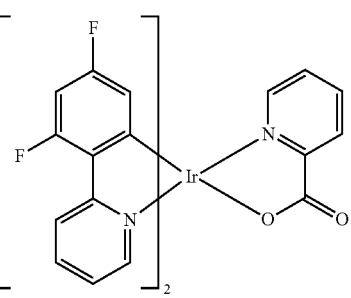 E-33
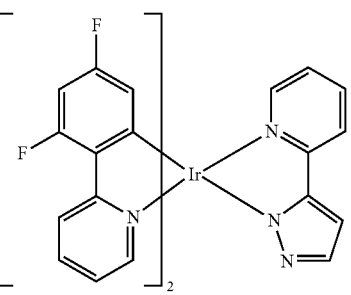 E-34
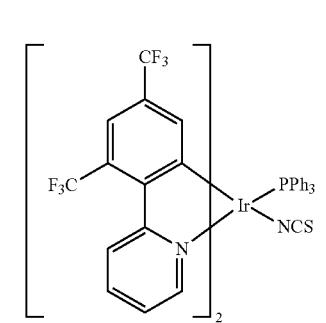 E-35
-continued
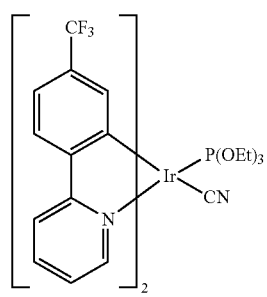 E-36
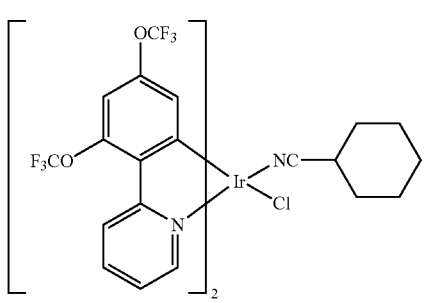 E-37
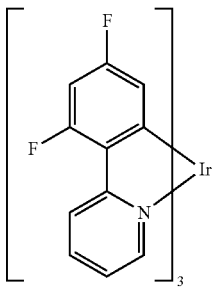 E-38
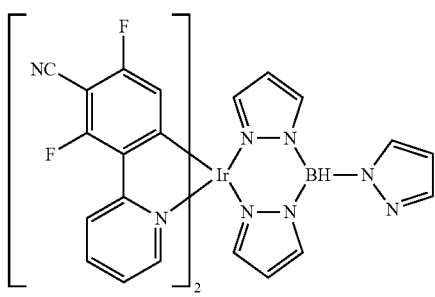 E-39
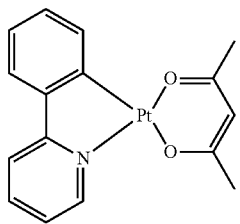 E-40

-continued

E-41

E-42

E-43

E-44

E-45

E-46

-continued

E-47

E-48

E-49

E-50

E-51

E-52

E-53

-continued
E-54
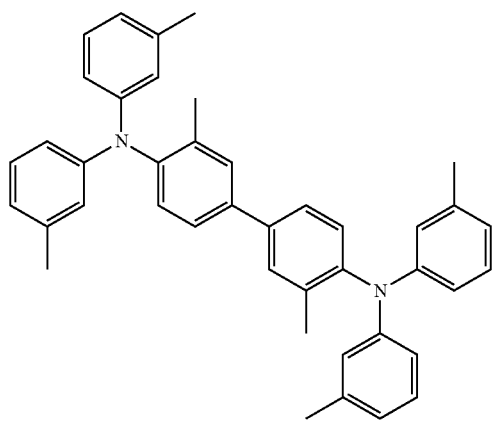
E-55
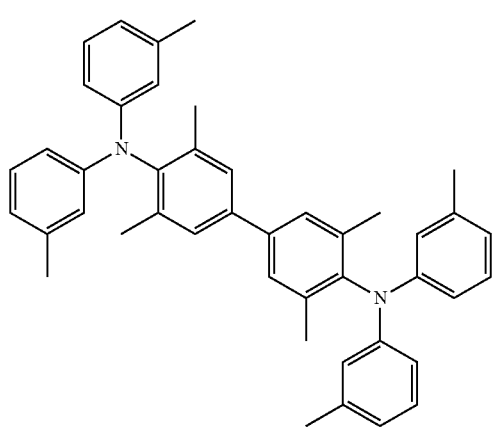
E-56
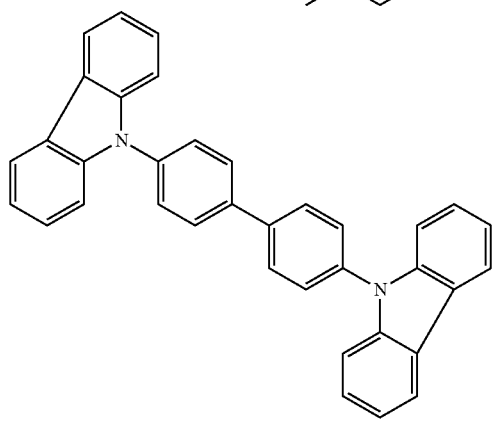
E-57
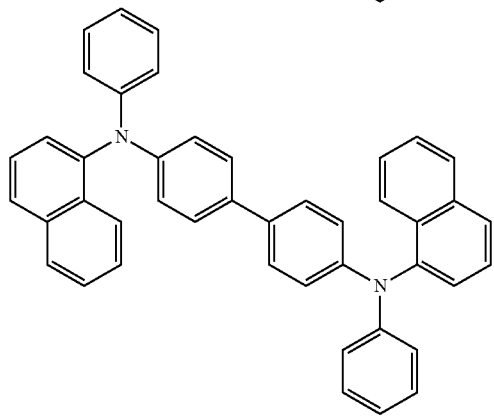
-continued
E-58
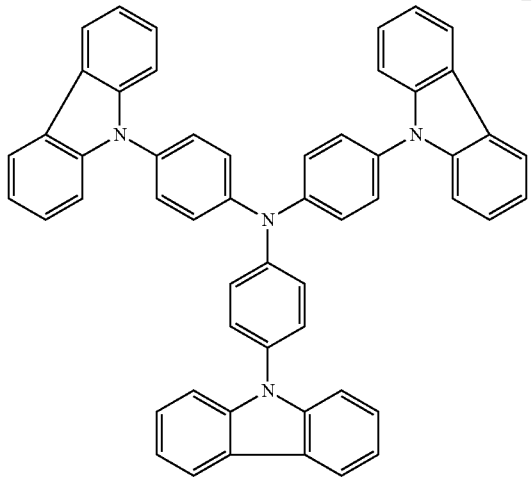
E-59
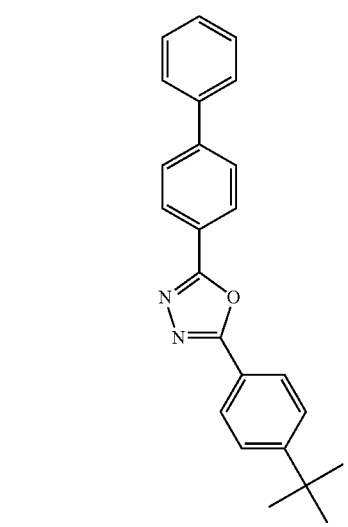
E-60
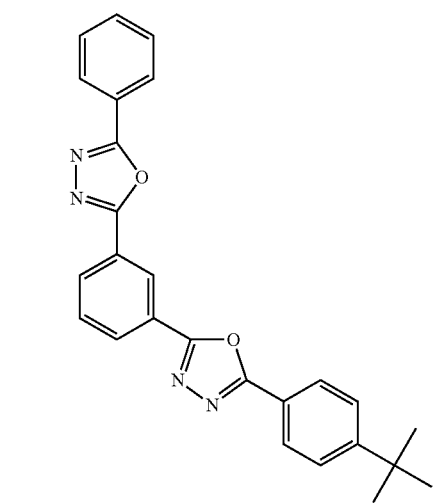

E-61 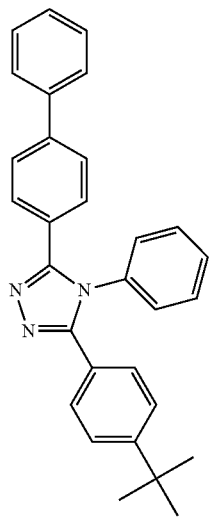

E-62 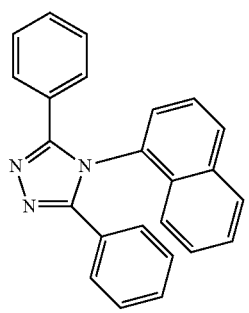

E-63 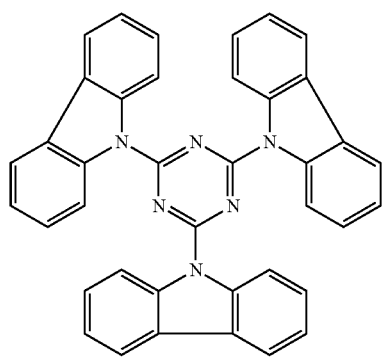

E-64 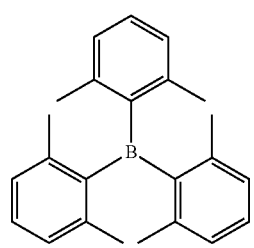

E-65 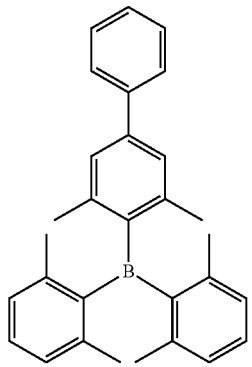

E-66 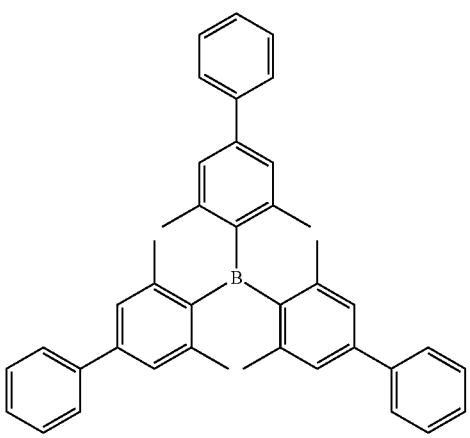

E-67 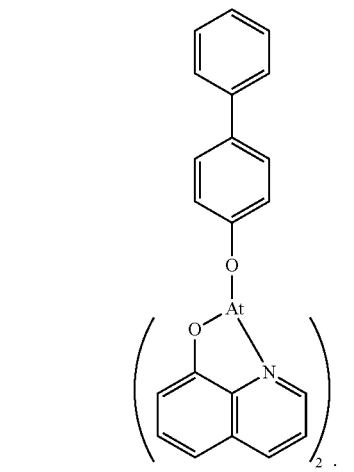

9. An organic electroluminescence device comprising a substrate, a pair of electrodes disposed on the substrate and, between the pair of electrodes, one or more organic layers having a luminescent layer, wherein the luminescent layer comprises the cyclic siloxane compound of claim 1.

10. An image display apparatus comprising the organic electroluminescence device of claim 9.

11. An area light source comprising the organic electroluminescence device of claim 9.

12. An organic electroluminescence device comprising a substrate, a pair of electrodes disposed on the substrate and, between the pair of electrodes, one or more organic layers having a luminescent layer, wherein the luminescent layer comprises the cyclic siloxane compound of claim 1 and an electron-transporting material, and said electron-transporting material being selected from the group consisting of a low molecular weight compound selected from the group consisting of an oxadiazole derivative, a triazole derivative, an imidazole derivative, a triazine derivative and a triarylborane derivative; a high molecular weight compound obtained by introducing polymerizable substituents into the low molecular weight compound followed by polymerizing; and a cyclic siloxane compound represented by Formula (1') below:

(1')

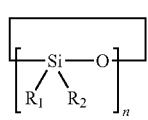

wherein, in Formula (1'), $R_1$ and $R_2$ are each independently a luminescent monovalent group, a charge-transporting monovalent group, or another substituent group; at least one of $R_1$ and $R_2$ is the charge-transporting monovalent group; and n is an integer of 2 to 100, wherein charge-transporting monovalent group is obtained by substituting a hydrogen atom of a charge-transporting compound represented by any one of Formulae (E-59) to (E-67) below with a linking group $X_B$, and is linked to a Si atom in Formula (1') via the linking group $X_B$:

E-59

E-60

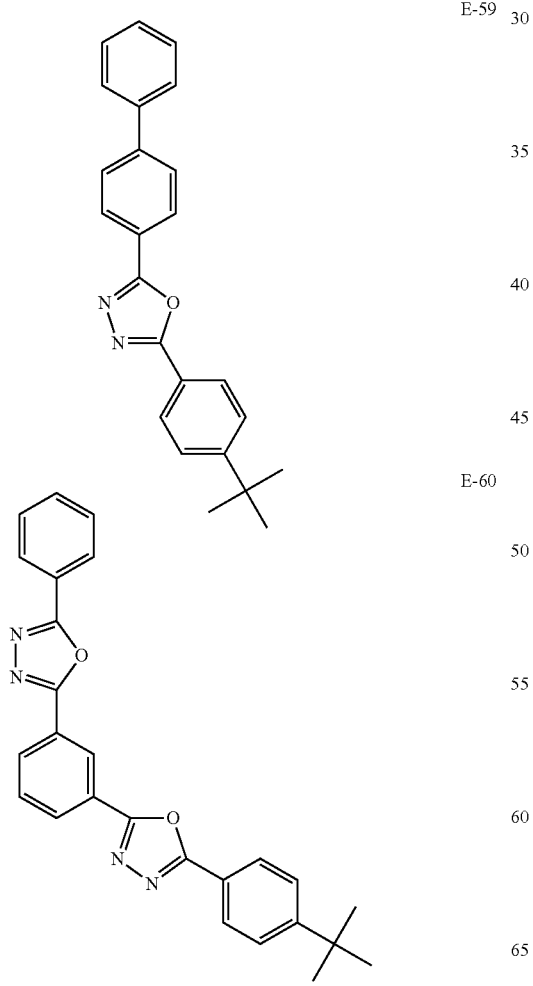

E-61

E-62

E-63

E-64

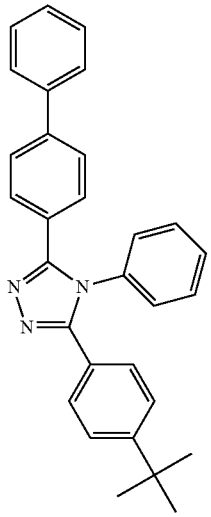

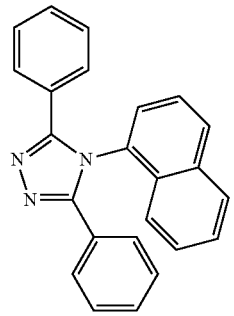

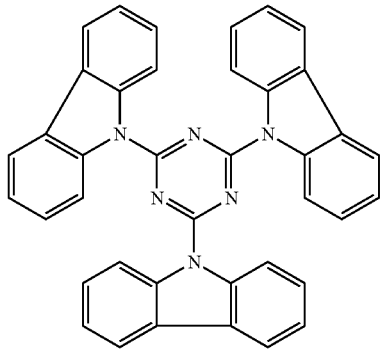

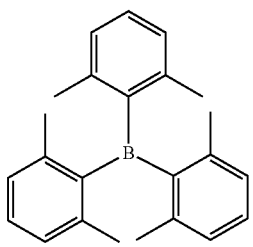

E-65
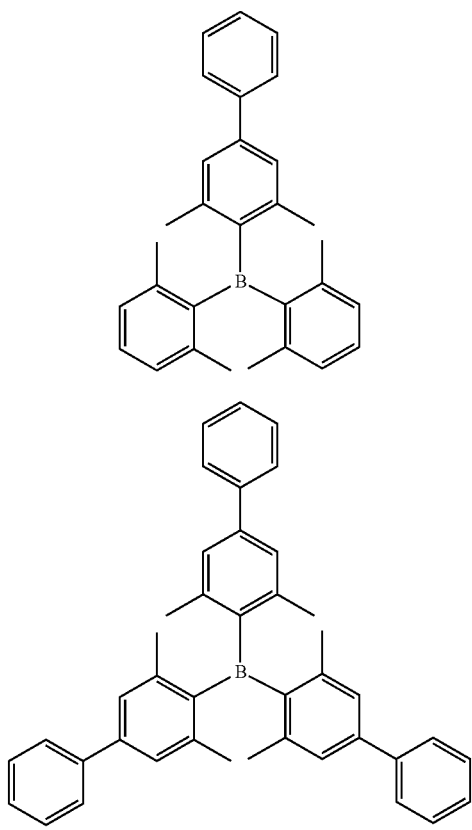
E-66
E-67
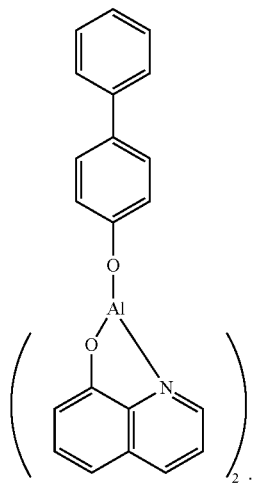
13. The cyclic siloxane compound according to claim 1, wherein n is an integer of 10 to 100.
14. The cyclic siloxane compound according to claim 1, wherein n is an integer of 30 to 100.
* * * * *